(12) United States Patent
Lee et al.

(10) Patent No.: US 12,064,285 B2
(45) Date of Patent: Aug. 20, 2024

(54) ULTRASOUND DIAGNOSTIC APPARATUS AND METHOD FOR CONTROLLING ULTRASOUND DIAGNOSTIC APPARATUS

(71) Applicant: SAMSUNG MEDISON CO., LTD., Gangwon-do (KR)

(72) Inventors: Sang Mok Lee, Seoul (KR); Hong Gyo Lee, Seoul (KR)

(73) Assignee: SAMSUNG MEDISON CO. LTD., Gangwon-do (KR)

( * ) Notice: Subject to any disclaimer, the term of this patent is extended or adjusted under 35 U.S.C. 154(b) by 115 days.

(21) Appl. No.: 17/437,921

(22) PCT Filed: Feb. 3, 2020

(86) PCT No.: PCT/KR2020/001580
§ 371 (c)(1),
(2) Date: Sep. 10, 2021

(87) PCT Pub. No.: WO2020/189890
PCT Pub. Date: Sep. 24, 2020

(65) Prior Publication Data
US 2022/0125406 A1 Apr. 28, 2022

(30) Foreign Application Priority Data
Mar. 15, 2019 (KR) .......................... 10-2019-0029719

(51) Int. Cl.
*A61B 8/00* (2006.01)

(52) U.S. Cl.
CPC .......... *A61B 8/4411* (2013.01); *A61B 8/4444* (2013.01); *A61B 8/461* (2013.01); *A61B 8/54* (2013.01)

(58) Field of Classification Search
CPC ..... A61B 8/4411; A61B 8/4444; A61B 8/461; A61B 8/54; A61B 8/4405; A61B 8/4477; A61B 8/467; A61B 8/4438
See application file for complete search history.

(56) References Cited

U.S. PATENT DOCUMENTS

| 10,226,229 B2 * | 3/2019 | Hongou .............. G01S 15/8927 |
| 2014/0350357 A1 * | 11/2014 | Lee ...................... A61B 8/4477 600/443 |

(Continued)

FOREIGN PATENT DOCUMENTS

| JP | 2013-027497 A | 2/2013 |
| KR | 10-2012-0059739 A | 6/2012 |

(Continued)

OTHER PUBLICATIONS

International Search Report dated Jun. 2, 2020 issued in International Patent Application No. PCT/KR2020/001580 (with English translation).

(Continued)

*Primary Examiner* — Alexei Bykhovski
(74) *Attorney, Agent, or Firm* — Morgan, Lewis & Bockius LLP

(57) ABSTRACT

An ultrasound diagnostic apparatus according to a disclosed embodiment comprises: a recognition information receiver for receiving recognition information from a probe; an input device for receiving a selection signal for the probe from a user; a probe select assembly (PSA) board including a connection module which is capable of mounting a probe connection module and a printed circuit board (PCB) which can electrically be connected to the probe connection module; and a controller for controlling the PSA board such that the probe connection module is connected to the PCB on the basis of the selection signal, and for controlling the probe on (Continued)

the basis of the connection between the probe connection module and the PCB.

11 Claims, 23 Drawing Sheets

(56) References Cited

U.S. PATENT DOCUMENTS

| | | | |
|---|---|---|---|
| 2016/0131746 A1 | 5/2016 | Beaty et al. | |
| 2016/0206284 A1* | 7/2016 | Lee | A61B 8/4477 |
| 2018/0064416 A1* | 3/2018 | Gu | A61B 8/429 |
| 2018/0228557 A1* | 8/2018 | Darisse | A61B 1/000094 |
| 2020/0076126 A1* | 3/2020 | Yang | H01R 12/79 |
| 2020/0275909 A1* | 9/2020 | Mniece | A61B 8/445 |

FOREIGN PATENT DOCUMENTS

| | | |
|---|---|---|
| KR | 10-2016-0089615 A | 7/2016 |
| KR | 10-2016-0099820 A | 8/2016 |
| KR | 10-2018-0070924 A | 6/2018 |

OTHER PUBLICATIONS

Chinese Office Action dated Feb. 7, 2024 issued in Chinese Patent Application No. 202080021564.7 (with English translation).
Korean Office Action dated Feb. 8, 2024 issued in Korean Patent Application No. 10-2019-0029719 (with English translation).

\* cited by examiner (a)                (b)

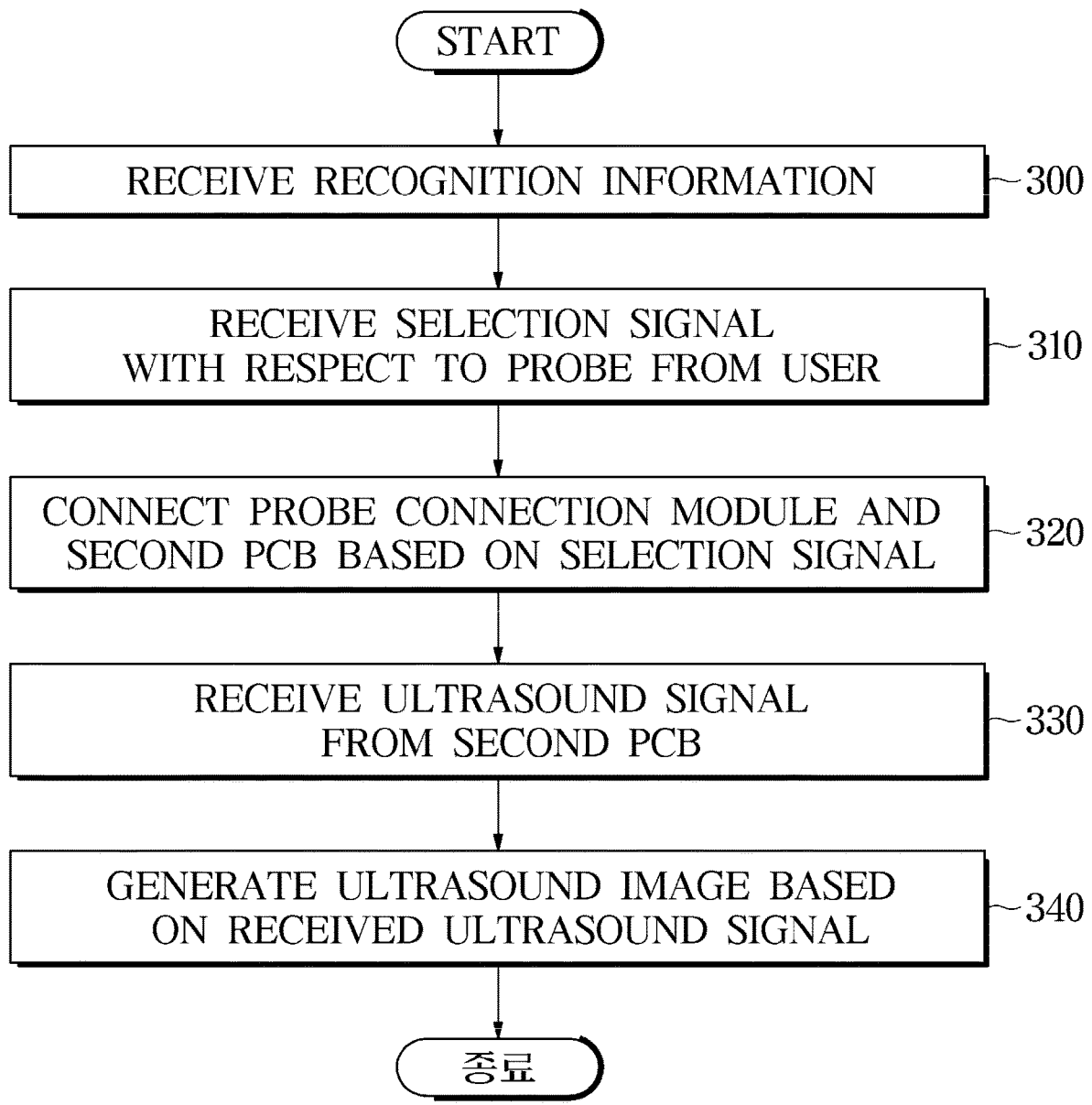

ULTRASOUND DIAGNOSTIC APPARATUS AND METHOD FOR CONTROLLING ULTRASOUND DIAGNOSTIC APPARATUS

CROSS-REFERENCE OF RELATED APPLICATIONS

This application is the U.S. National Phase under 35 U.S.C. § 371 of International Patent Application No. PCT/KR2020/001580, filed on Feb. 3, 2020, which in turn claims the benefit of Korean Application No. 10-2019-0029719, filed on Mar. 15, 2019, the entire disclosures of which applications are incorporated by reference herein.

TECHNICAL FIELD

Embodiments set forth herein relate to an ultrasound diagnostic apparatus for receiving an ultrasound image from a probe and a control method thereof.

BACKGROUND ART

An ultrasound diagnostic apparatus emits an ultrasound signal, which is generated from a transducer of a probe, to a subject and receives information of a signal reflected from the subject to obtain at least one image of an inner part (e.g., soft tissue or a blood flow) of the subject.

The ultrasound diagnostic apparatus is compact, inexpensive, and has non-invasive and non-destructive characteristics when compared to other diagnostic imaging devices, such as an X-ray machine, a computerized tomography (CT) scanner, a magnetic resonance imaging (MRI) device, or a nuclear medicine diagnosis device, and thus has been widely used to diagnose heart disease, abdominal disease, urinary organ disease, etc., including an obstetrics and gynecological diagnosis.

The ultrasound diagnostic apparatus includes a main body accommodating main components thereof, and a probe that includes a probe unit for transmitting an ultrasound signal to a subject and receiving an echo ultrasound signal reflected from the subject to obtain an ultrasound image of the subject, and a probe connector configured to be connected to the main body.

DISCLOSURE

Technical Problem

An aspect of an embodiment set forth herein relates to an ultrasound diagnostic apparatus in which an additional printed circuit board (PCB) module is employed to allow a mechanical connection/disconnection between ultrasound waves and a probe and a relay used in the related art is omitted, and a control method thereof.

Technical Solution

According to an embodiment, an ultrasound diagnostic apparatus includes a recognition information receiving unit configured to receive recognition information from a probe, an input device configured to receive a selection signal with respect to the probe from a user, a probe select assembly (PSA) board including a connection module configured to mount a probe connection module thereon and a printed circuit board (PCB) configured to be electrically connected to the probe connection module, and a controller configured to control the PSA board so as to connect the probe connection module to the PCB on the basis of the selection signal and control the probe on the basis of a connection between the probe connection module and the PCB.

The probe connection module may include a female connector configured to accommodate a male connector connected to the probe, and a sub PCB to which the female connector is attached.

The connection module may include a moving part configured to move the probe connection module through an actuator.

The PCB may include a connection pin configured to allow the PCB to be electrically connected to the sub PCB.

The connection module may include a connection pin configured to allow the connection module to be electrically connected to the sub PCB.

The sub PCB may include a connection pin configured to allow the sub PCB to be electrically connected to the PCB.

The actuator may be provided on the PSA board and configured to move the probe connection module on the basis of at least one of an electromagnet, a motor, hydraulic pressure, or pneumatic pressure.

The PCB may have an area greater than or equal to an area of the sub PCB.

The connection module may be provided to be rotated on the PCB to separate the probe connection module.

The controller may divide and connect channel elements on the basis of a plurality of pieces of recognition information.

The ultrasound diagnostic apparatus may further include a display displaying the recognition information, and the controller may control the display to display the recognition information.

The sub PCB may have an area greater than or equal to an area of the female connector.

According to another embodiment, a control method of an ultrasound diagnostic apparatus includes receiving probe recognition information from at least one probe, receiving a selection signal from a user, controlling a probe select assembly (PSA) board to connect a probe connection module to a main printed circuit board (PCB) on the basis of the selection signal, controlling a probe selected on the basis of a connection between the probe connection module and the main PCB, and receiving an ultrasound signal from the probe through the PSA board.

The controlling of the PSA board may include moving the probe connection module through a moving part provided on the connection module.

The controlling of the PSA board may include connecting the probe connection module to a sub PCB on the basis of movement of the moving part provided on the connection module.

The controlling of the PSA board may include moving the probe connection module to the main PCB through an actuator.

The controlling of the probe may include transmitting a control signal to the probe through the PSA board on the basis of a connection between the probe connection module and the main PCB.

The receiving of the ultrasound signal may include controlling the PSA board to transmit an echo ultrasound signal transmitted from the probe to a beamformer.

The control method may further include generating an ultrasound image through the beamformer and a signal processor and displaying the generated ultrasound image.

The control method may further include checking a connection status between the probe connection module and the probe on the basis of the recognition information.

Advantageous Effects

In an aspect, in an ultrasound diagnostic apparatus and a control method thereof, an additional printed circuit board (PCB) is employed to enable a mechanical connection/disconnection between ultrasound waves and a probe, and a relay used in the related art can be omitted.

In another aspect, in an ultrasound diagnostic apparatus and a control method thereof, only a probe selected by a user from among a plurality of probes can be electrically connected to while disconnecting the other probes.

In another aspect, in an ultrasound diagnostic apparatus and a control method thereof, a relay can be omitted to reduce design complexity and increase utilization of a space due to the omission of the relay.

In another aspect, in an ultrasound diagnostic apparatus and a control method thereof, connection can be made through a probe and a connector that are used in the related art and device compatibility can be achieved.

DESCRIPTION OF DRAWINGS

FIG. 15 is a flowchart of a control method of an ultrasound diagnostic apparatus according to an embodiment.

MODES OF THE INVENTION

Figure 1:
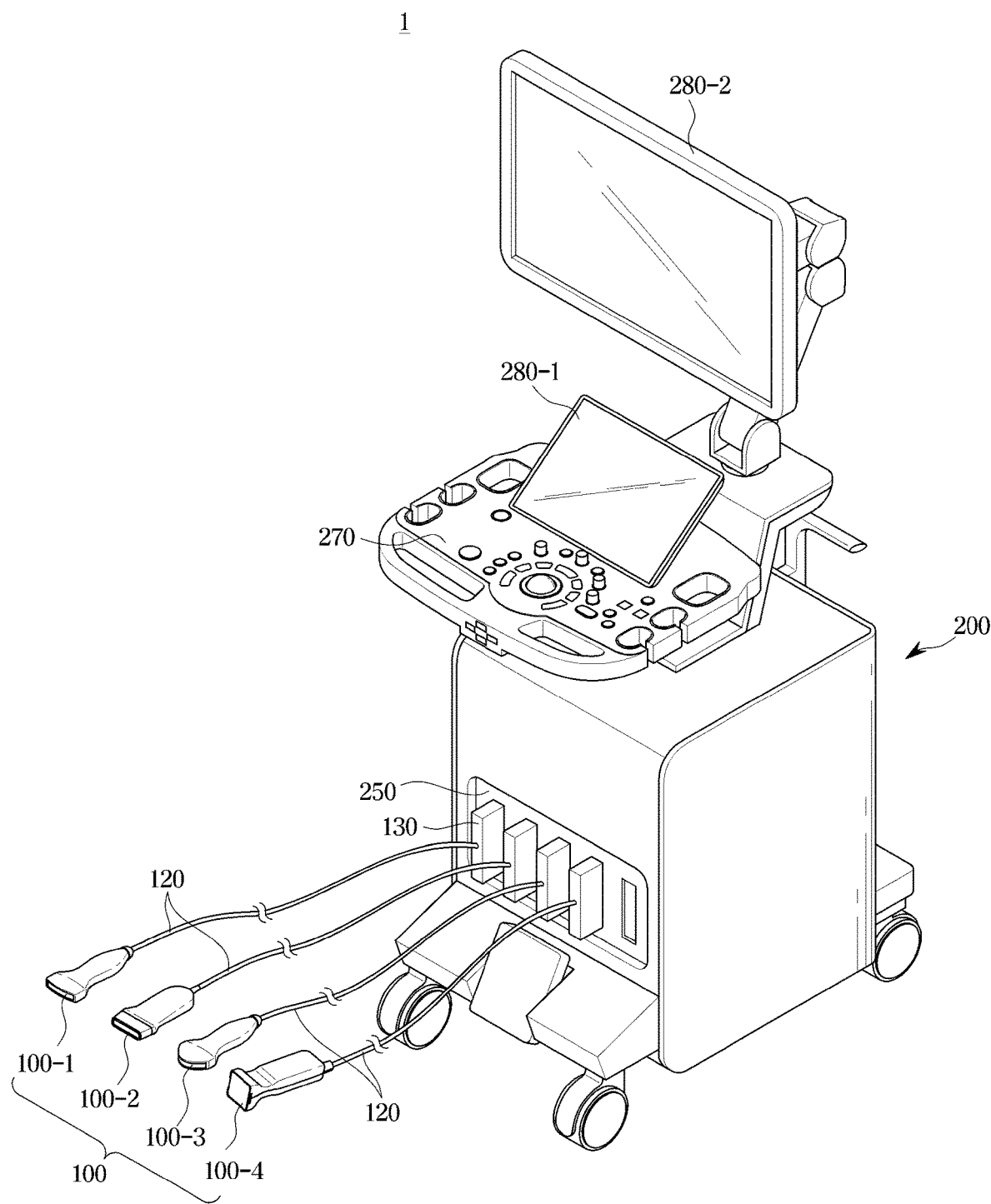
FIG. 1 is a perspective view of the external appearance of an ultrasound diagnostic apparatus according to an embodiment.

The same reference numerals refer to the same elements throughout the specification. The present specification does not describe all elements of embodiments, and a description of general matters in the technical field to which the present disclosure pertain or the same matters in the embodiments will be omitted herein. Terms such as "unit", "module", "member", and "block" used herein may be embodied as software or hardware components, and according to an embodiment, a plurality of units, modules, members, or blocks may be embodied together as one component or one unit, module, member or block may include a plurality of components.

Throughout the specification, when an element is referred to as being "connected to" another element, the element should be understood as being connected directly or indirectly to the other element or the indirect connection should be understood to include connection through a wireless communication network.

It will be understood that when an element is referred to as "including" another element, the element may further include other elements unless mentioned otherwise.

Throughout the present specification, when an element is referred to as being "on" another element, it should be understood that the element is in contact with the other element or another element is present therebetween.

Terms such as first and second are used to distinguish one component from another component and components are not limited by these terms.

As used herein, the singular expressions are intended to include plural forms as well, unless the context clearly dictates otherwise.

Reference numerals assigned to operations are used only for convenience of description rather than describing an order of the operations and thus these operations may be performed in an order different from that described above unless the context indicates a specific order.

Hereinafter, a principle of operation of the present disclosure and embodiments will be described with reference to the accompanying drawings.

Figure 2:
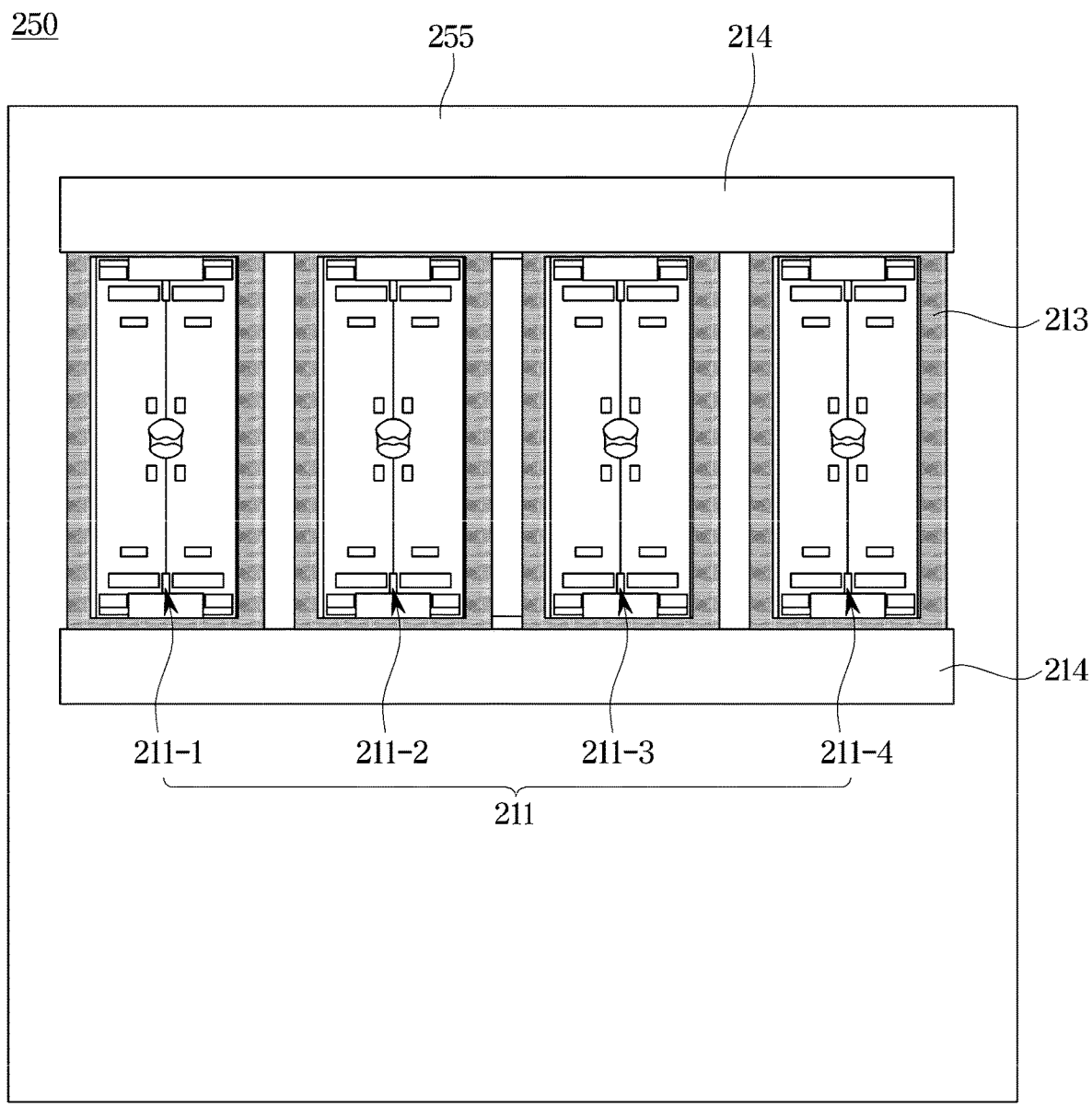
FIG. 2 is a front view of a probe select assembly (PSA) board according to an embodiment.
Figure 3:
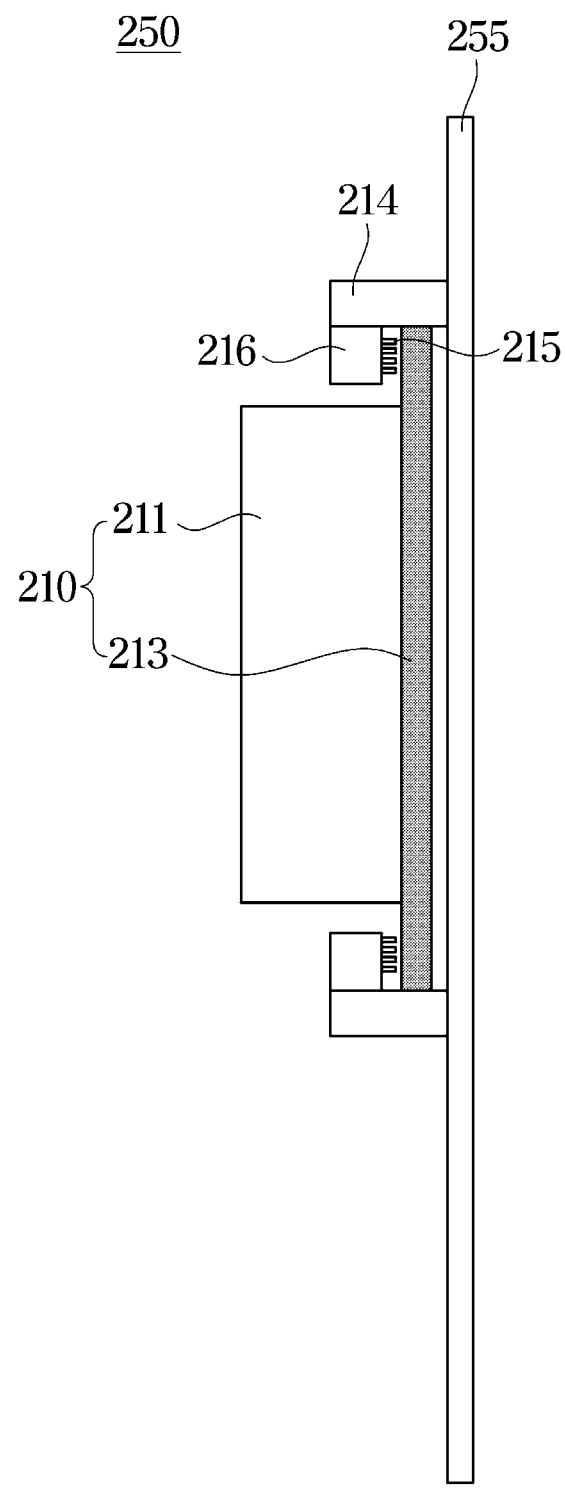
FIG. 3 is a side view of the PSA board.

FIG. 1 is a perspective view of the external appearance of an ultrasound diagnostic apparatus according to an embodiment. FIG. 2 is a front view of a probe select assembly (PSA) board according to an embodiment. FIG. 3 is a side view of the PSA board. FIGS. 1 to 3 will be described together below to avoid a redundant description.

As shown in FIG. 1, an ultrasound diagnostic apparatus 1 includes a main body 200, and a probe 100 for transmitting an ultrasound signal to or receiving an ultrasound signal from a subject to be diagnosed.

Here, the subject may refer to a human or an animal having blood vessels but is not limited thereto, and anything may be the subject provided an image of an internal structure thereof can be captured by an ultrasound diagnostic apparatus.

The probe 100 emits ultrasound waves to the subject, receives echo ultrasound waves reflected from the subject, and converts the echo ultrasound waves into an electrical signal (hereinafter referred to as an ultrasound signal). The probe 100 transmits the ultrasound signal to the main body 200 through a cable 120.

The main body 200 includes a PSA board 250 connected to the probe 100, displays 280-1 and 280-2 displaying an ultrasound image converted from an ultrasound signal received from the probe 100, and an input device 270 for receiving various commands input from a user.

As shown in FIG. 1, a plurality of probes 100-1 to 100-4, 100 may be connected to the PSA board 250. The main body 200 is connected to one or more probes selected by a user through the PSA board 250 described below. This will be described in detail with reference to other drawings below.

Although FIG. 1 illustrates that four probes are connected, the number of probes to be connected is not limited to four and the ultrasound diagnostic apparatus 1 may be connected to various numbers of probes 100 in various forms.

As shown in FIG. 2, the PSA board 250 according to an embodiment may include a main printed circuit board (PCB) 255 capable of receiving an ultrasound signal from the probe 100 and a connection module 214 for connecting the main PCB 255 and a sub PCB 213.

Here, the sub PCB 213 may be provided to be coupled with a female connector 211, thus forming a probe connection module 210. That is, the sub PCB 213 may be attached to the female connector 211 to form a module. The sub PCB 213 and the female connector 211 forming the module may be mounted on the PSA board 250 and may be attached or detached by a user.

The sub PCB 213 may function as a path of various signals such as a control signal and an ultrasound signal when connected to the main PCB 255 through the connection module 214. Hereinafter, the sub PCB 213 will be referred to as a first PCB, and the main PCB 255 will be referred to as a second PCB.

The female connector 211 among a plurality of female connectors 211-1, 211-2, 211-3 and 211-4 may be connected to and locked with a male connector 130 connected to the probe 100.

The probe connection module 210 may be mounted simply on the PSA board 250 but may not be electrically connected to the PSA board 250. The PSA board 250 electrically connects the first PCB 213 and the second PCB 255 under control of the connection module 214.

As shown in FIG. 3, the connection module 214 may be provided on the second PCB 255. The connection module 214 may include a connection pin 215, and a moving part 216 for moving the probe connection module 210.

Specifically, the connection pin 215 serves as a point of contact for connection of the first PCB 213 and the second PCB 255.

The moving part 216 moves the probe connection module 210 mounted on the connection module 214. Various embodiments in which the first PCB 213 and the second PCB 255 are electrically connected will be described with reference to the drawings below.

When the first PCB 213 and the second PCB 255 are electrically connected, the second PCB 255 transmits an ultrasound signal, which is transmitted from the probe 100, to a beamformer 290 included in the main body 200. In addition, the second PCB 255 may transmit a control signal, which is generated by the controller 260 to control the probe 100, to the probe 100.

The input device 270 illustrated in FIG. 1 includes a control panel for receiving a command input from a user to control the ultrasound diagnostic apparatus 1 and various types of hardware components.

The input device 270 may receive, from a user, a selection signal for selecting one of a plurality of probes and various control commands such as a command to configure the probe 100 and a command to operate the main body 200 for generation of an ultrasound image.

The input device 270 may be embodied as various types of hardware devices such as a keyboard, a foot switch, or a foot pedal. For example, when the input device 270 is embodied as a keyboard, the keyboard may include at least one of a switch, a key, a joystick, and a trackball. As another example, the keyboard may be embodied as software such as a graphical user interface. In this case, the keyboard may be displayed through the sub-display 280-1. The foot switch or the foot pedal may be provided at a lower portion of the main body 200, and a user may control an operation of the ultrasound diagnostic apparatus 1 using the foot pedal.

A display 280 may display an ultrasound image generated by the main body 200 and various graphical user interfaces.

For example, the display 280 may include the first display 280-1 and the second display 280-2.

Specifically, the ultrasound image displayed on the first display 280-1 may be a two-dimensional (2D) ultrasound image or a three-dimensional (3D) ultrasound image, and various ultrasound images may be displayed according to an operating mode of the ultrasound diagnostic apparatus 1. In addition, the first display 280-1 may display not only a menu or guide necessary to make an ultrasound diagnosis but also information about an operational state of the probe 100.

The second display 280-2 may provide relevant information such as a menu or an auxiliary image for optimizing an ultrasound image or provide a user with a graphical user interface. When the second display 280-2 functions as the input device 270, the second display 280-2 may display a graphical user interface having the same shape as buttons included in the input device 270.

The display 280 may be embodied as well-known various forms such as a cathode ray tube (CRT), a liquid crystal display (LCD), a light-emitting diode (LED), a plasma display panel (PDP), and an organic LED (OLED). When the display 280 performs a function of the input device 270, the display 280 may include a touch screen panel.

In addition, the ultrasound diagnostic apparatus 1 may include other various components that are not described herein.

Figure 4A:
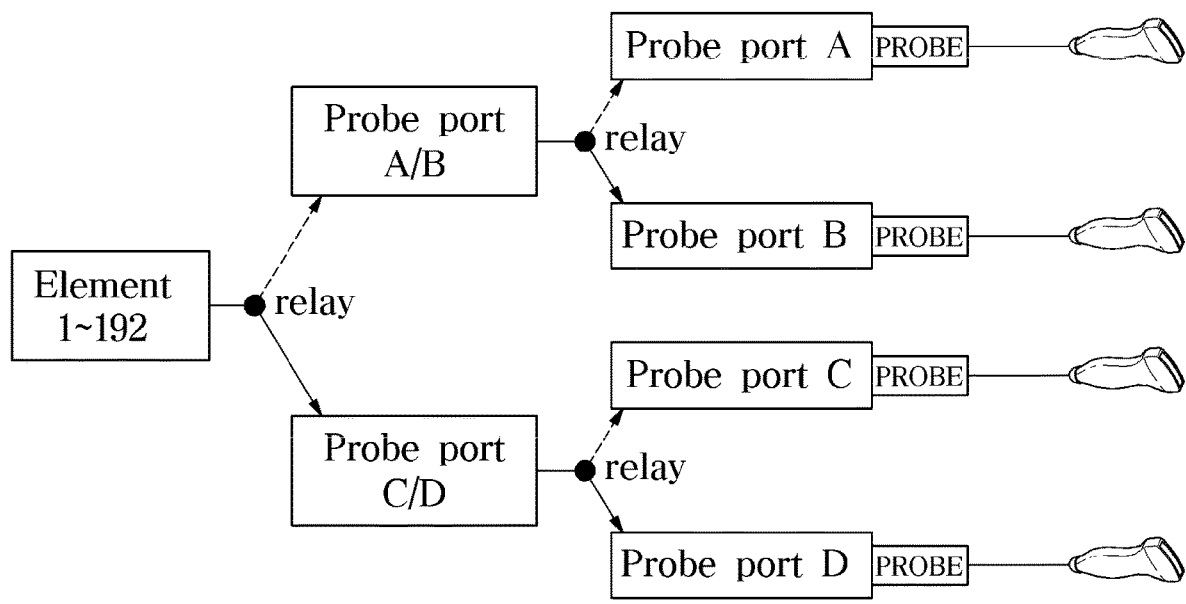
FIGS. 4A and 4B are block diagrams of PSA boards including a relay according to the related art.
Figure 4B:
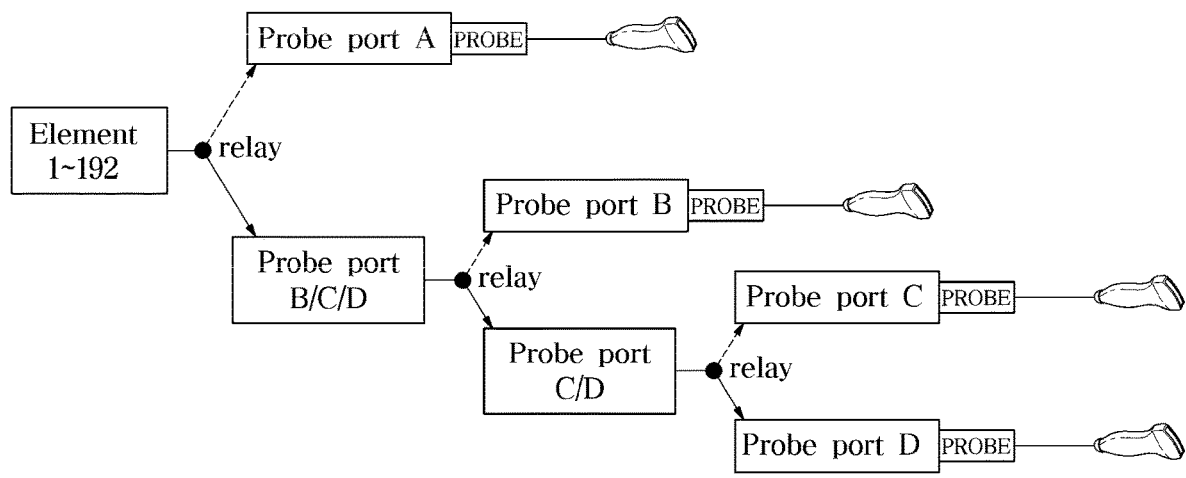

FIGS. 4A and 4B are block diagrams of PSA boards including a relay according to the related art.

A PSA board of the related art uses several hundreds of relays to connect a probe, which is selected by a user from among a plurality of probes, and a main body to enable exchange of electrical signals therebetween.

As shown in FIGS. 4A and 4B, up to three relays are needed to connect one element to four probe connection ports A, B, C and D. Thus, about 300 relays are required in the PSA board of the related art in which a two-channel relay is used to connect general 192 element probes to the main body having four probe connection ports.

Similarly, the PSA board of the related art uses a PCB to implement relays of FIG. 4A or 4B. In the PSA board of the related art, the number of layers of the PCB and the number of relays are exponentially increased to increase the number of probe connection ports. Furthermore, in order to fabricate such a PCB, size constraints, circuit complexity, and interference between signals are unavoidable and thus the quality of an image may decrease. When such hardware aspects are considered, only up to four probe connection ports are provided in most of general ultrasound diagnostic apparatuses of the related art.

The PSA board 250 does not use a relay and connects the first PCB 213 and the second PCB 255 to a probe selected by a user through the connection module 214, thereby disconnecting the other probes that are not to be used. The PSA board 250 may further include a probe connection port in a space of the main body 200, which is occupied by relays in the case of the related art. By omitting relays in the PSA board 250, circuit complexity may be reduced and image quality may be increased.

Figure 5:
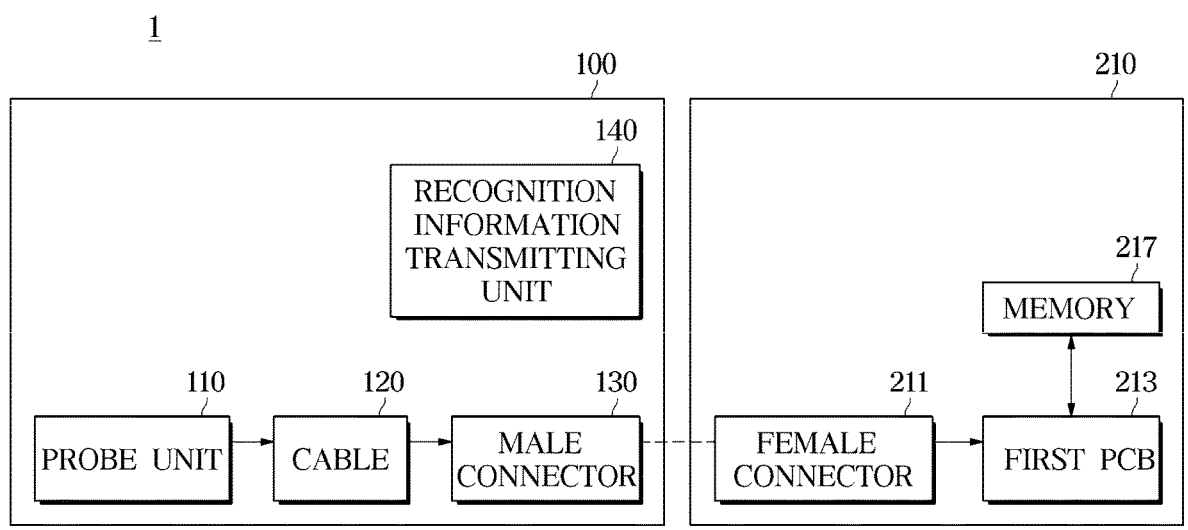
FIG. 5 is a control block diagram for describing a probe and a probe connection module.
Figure 6:
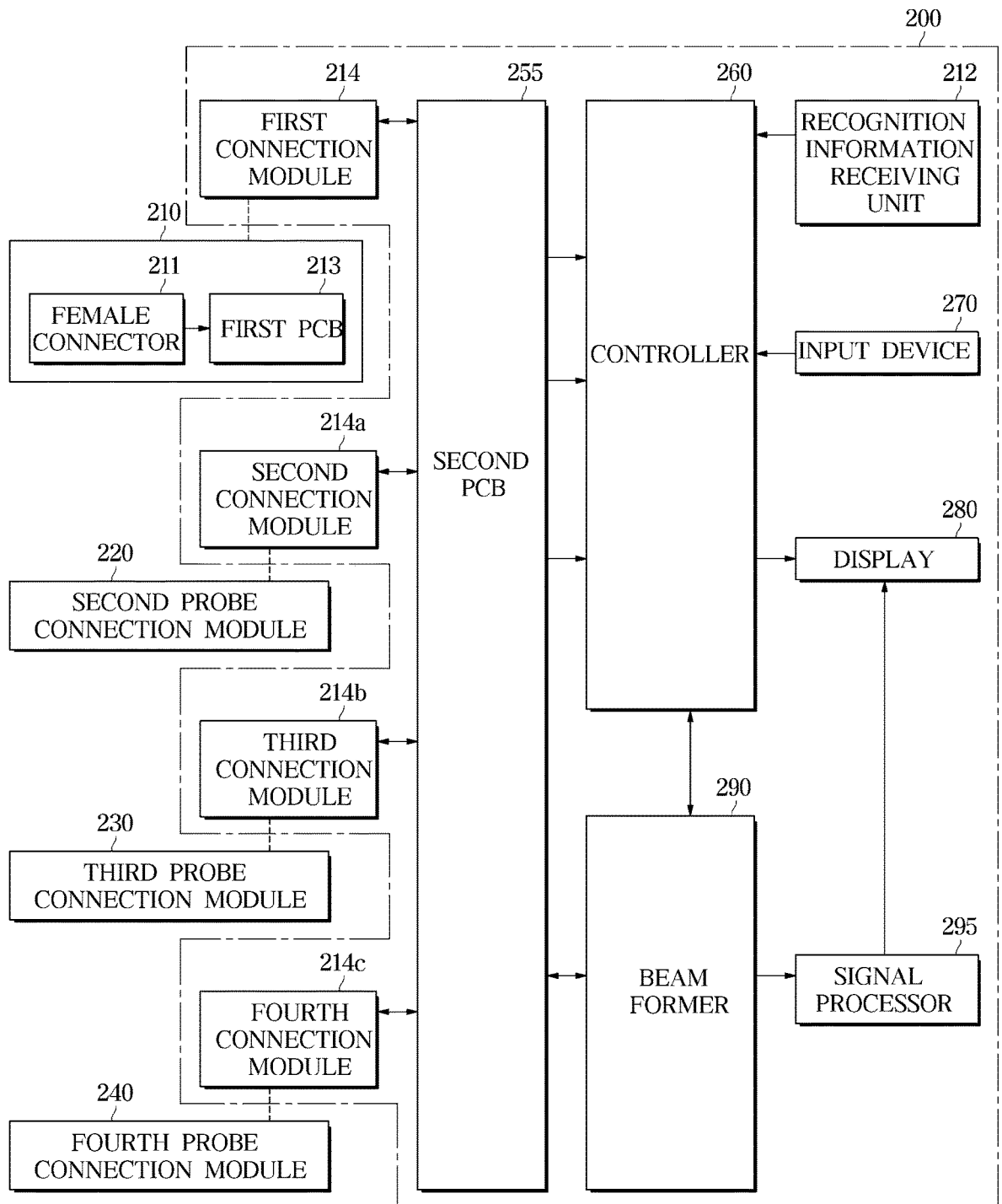
FIG. 6 is a control block diagram of a main body of an ultrasound diagnostic apparatus according to an embodiment.

FIG. 5 is a control block diagram for describing a probe and a probe connection module. FIG. 6 is a control block diagram of a main body of an ultrasound diagnostic apparatus according to an embodiment. FIGS. 5 and 6 will be described together below to avoid a redundant description.

As shown in FIG. 5, a probe 100 includes a probe unit 110 configured to be in direct contact with a subject, a male connector 130 for transmitting a signal to or receiving a signal from a main body 200, a cable 10 for connecting the probe unit 110 and the male connector 130, and a recognition information transmitting unit 140 for transmitting recognition information to the main body 200.

Specifically, the probe unit 110 includes a transducer (not shown) for converting an electrical signal into vibration energy or converting vibration energy into an electrical signal, and the transducer may transmit ultrasound waves to a subject or receive an echo ultrasound waves from the subject using an oscillator such as a piezoelectric elements (not shown).

When the number of elements of the transducer is 192, about 300 2-channel relays are needed in a PSA board of the related art.

The probe unit 110 may be provided as a linear probe unit having a linear surface (see 100-1), a convex probe unit (see 100-3) having a convex curved surface, and a matrix probe unit (see 100-4) according to an arrangement of transducer modules, as illustrated in FIG. 1. However, embodiments are not limited thereto, and the probe unit 110 may be provided in other forms, e.g., a phase array probe, which are known in the art, as well as those illustrated in FIG. 1.

The probe unit 110 may be connected to one end of the cable 120, and the male connector 130 may be connected to another end of the cable 120.

The male connector 130 may be mounted or locked after being inserted into a female connector 211. When a first PCB 213 and a second PCB 255 are electrically connected, the male connector 130 transmits an ultrasound signal to or receives an ultrasound signal from the probe connection module 210 or transmits or receives a control signal generated by the main body 200.

The recognition information transmitting unit 140 transmits recognition information to the main body 200.

Here, the recognition information includes all information related to the probe 100 and, particularly, probe identification information such as probe model information, version information, and a serial number. For example, the first to fourth probes 100-1 to 100-4 may include different recognition information, and the main body 200 may identify the first to fourth probes 100-1 to 100-4 according to recognition information.

The recognition information transmitting unit 140 may be embodied as a conductive point-of-contact mount and provided on one end of the male connector 130. When the conductive point-of-contact mount is in contact with the female connector 211, the recognition information transmitting unit 140 may exchange recognition information with a recognition information receiving unit 212 through wireless communication.

The recognition information transmitting unit 140 and the recognition information receiving unit 212 described below may be implemented as a wireless communication module.

The probe 100 may include various components such as a processor for processing data and a memory storing data, as well as the above-described components.

Various probe connection modules 210, 220, 230, and 240 according to the embodiment connect the probe 100 and the main body 200. The probe connection modules 210, 220, 230, and 240 may be configured independently of the main body 200 and may be separated from the main body 200 and replaced with other probe connection modules by a user.

The probe connection modules 210, 220, 230, and 240 may include components such as the female connector 211, the first PCB 213, or a memory 217.

The female connector 211 is mechanically coupled with the male connector 130 to accommodate the male connector 130. The female connector 211 includes a hardware device configured to hold and lock the male connector 130 after the male connector 130 is inserted into the female connector 211. Locking performed by the female connector 211 may be manually performed by a user or may be automatically performed through various types of locking devices.

The first PCB 213 may be coupled to the female connector 211 and the memory 217 and may form an electrical point of contact with the second PCB 255 or a plurality of connection pins 215 of a connection module 214.

An area of the first PCB 213 may be greater than or equal to that of the female connector 211. A plurality of connection pins (not shown) may be provided in a region of the first PCB 213 in which the female connector 211 is not accommodated. The plurality of connection pins provided in the first PCB 213 may form a point of contact with the connection pins 215 of the connection module 214 or the second PCB 255.

The memory 217 refers to a storage medium including a non-volatile memory device and may store information indicating configurations of the probe connecting modules 210, 220, 230 and 240. When the first PCB 213 is connected to the second PCB 255, the information stored in the memory 217 is transmitted to the main body 200 and a user is able to check the configurations of the combined probe connection modules 210, 220, 230 and 240 through the display 280.

The memory 217 according to an embodiment may include an electrically erasable programmable ROM (EEPROM) but is not necessarily limited thereto and may be embodied as another storage medium such as an erasable programmable ROM (EPROM).

A total number and form of the probe connection modules 210, 220, 230, and 240 connected to the main body 200 may vary according to the shapes of the connection module 214 and the second PCB 255. That is, the number of probe connection modules 210, 220, 230 and 240 to be connected to the main body 200 is illustrated as four in FIG. 6 but is not necessarily limited to four.

The main body 200 includes the recognition information receiving unit 212 for receiving recognition information, the connection module 214 for connecting the first PCB 213 and the second PCB 255, the second PCB 255 to which the connection module 214 is attached, an input device 270 for receiving a command input from a user, a beamformer 290 for receiving an ultrasound signal from the second PCB 255, a signal processor 295 for enhancing the quality of an ultrasound image on the basis of a signal transmitted from the beamformer 290, a display 280 displaying the ultrasound image processed by the signal processor 295, and a controller 260 for controlling the above components.

The recognition information receiving unit 212 may be included inside the main body 200 to receive recognition information from the recognition information transmitting unit 140. The recognition information receiving unit 212 may convert the received recognition information into an electrical signal and transmit the electrical signal to the controller 260.

The recognition information receiving unit 212 may include various types of communication modules to receive signals transmitted from the recognition information transmitting unit 140. Specifically, the recognition information receiving unit 212 may include at least one of a short-range communication module, a wired communication module, and a wireless communication module.

The short-range communication module may include various types of short-range communication module for transmitting or receiving a signal using a wireless communication network within a short range, e.g., a Bluetooth module, an infrared communication module, a radio frequency identification (RFID) communication module, a wireless local access network (WLAN) communication module, a near-field communication (NFC) module, a ZigBee communication module, etc.

The wireless communication module may include a Wi-Fi module, a wireless broadband (WiBro) module, and wireless communication modules supporting various wireless communication methods such as Global System for Mobile Communications (GSM), Code Division Multiple Access (CDMA), Wideband Code Division Multiple Access (WCDMA), Universal Mobile Telecommunications System (UMTS), Time Division Multiple Access (TDMA), and Long-Term Evolution (LTE).

The recognition information receiving unit 212 may further include a wireless communication interface including an antenna and a receiver for receiving a signal including recognition information. The recognition information receiving unit 212 may further include a signal conversion module for demodulating a radio signal, which is an analog signal received through the wireless communication interface, into a digital control signal.

Connecting modules 214, 214a, 214b, and 214c are hardware devices that allow probe connection modules 210, 220, 230, 240 to be mounted on the main body. In addition, the connection modules 214, 214a, 214b, and 214c respectively electrically connect the probe connection modules 210, 220, 230 and 240 to the second PCB 255 through an operation described below.

Specifically, the connection modules 214, 214a, 214b, and 214c include a moving part 216 for moving the probe connection modules 210, 220, 230, and 240. The moving part 216 may be operated by a hardware device such as an actuator, and the probe connection modules 210, 220, 230 and 240 and the second PCB 255 may be electrically connected through various operations of the moving part 216. An embodiment of various operations of the moving part 216 will be described with reference to other drawings below.

The actuator may use at least one of an electromagnet, a motor, hydraulic pressure, and pneumatic pressure.

The second PCB 255 is connected to a probe connection module selected from among the probe connection modules 210, 220, 230 and 240 on the basis of a selection signal from a user. The second PCB 255 transmits ultrasound signals transmitted from the connected probe connection modules 210, 220, 230 and 240 to the controller 260 or the beamformer 290.

The second PCB 255 may be provided at one side of the main body 200 and may be attached to the connection modules 214, 214a, 214b, and 214c, the total number and form of which are variable.

Similar to the probe connection modules 210, 220, 230, and 240, the number of connection modules 214, 214a, 214b, and 214c attached to the second PCB 255 is not limited to four and may be changed variously.

The controller 260 is configured to control the ultrasound diagnostic apparatus 1 and is a processor that controls overall operations of various components such as the recognition information receiving unit 212, the connection module 214, the display 280, the beamformer 290, and the signal processor 295.

The controller 260 operates the ultrasound diagnostic apparatus 1 on the basis of a command input from a user, which is received through the input device 270. As an example, when the input device 270 receives a selection signal for selecting the probe 100 from a user, the controller 260 determines the connection module 214, 214a, 214b or 214c to be operated on the basis of the recognition information and the selection signal. The controller 260 controls the connection module 214 to connect the first PCB 213 included in the determined probe connection module 210, 220, 230 or 240 and the second PCB 255 included in the main body 200.

The controller 260 controls the probe 100 through a probe connection module connected to the second PCB 255. Specifically, the controller 260 may control a probe unit 110 to form ultrasound signals to be supplied to a plurality of transducers included in the probe 100 by taking into consideration the positions of the plurality of transducers and a point of contact.

The controller 260 may receive an echo ultrasound signal, which is reflected from a subject, from the probe 100 and control the display 280 to display an ultrasound image generated through the beamformer 290 and the signal processor 295.

The controller 260 may include a read-only memory (ROM) storing a control program for controlling the ultrasound diagnostic apparatus 1 and a random access memory (RAM) used as a storage area corresponding to various operations performed by the ultrasound diagnostic apparatus 1. The controller 260 may be embodied as a processing board (graphics processing board) including a processor, a RAM, or a ROM as described above and mounted on a circuit board, and the processor, the RAM, and the ROM may be connected to one another through an internal bus.

An embodiment of a control method of the controller 260 will be described in detail with reference to other drawings below.

The beamformer 290 is a device that delays ultrasound waves to be emitted or echo ultrasound waves to be received for an appropriate time so as to allow ultrasound waves generated by the probe unit 110 to be simultaneously focused on a target point on a subject at a desired point in time or remove the difference between times when echo ultrasound waves reflected from the target point on the subject reach the probe unit 110.

In order to enhance the quality of an ultrasound image, the signal processor 295 filters a noise component from a focused digital reception beam and performs envelope detection to detect the intensity of a received signal on the basis of the filtered focused digital reception beam so as to generate a digital ultrasound image data.

The signal processor 295 may perform scan conversion to convert a scan line of the digital ultrasound image data so that the digital ultrasound image data may be displayed on the display 280, and perform image processing such as B-mode image processing and Doppler image processing on the digital ultrasound image data so that a user's desired ultrasound image is displayed on the basis of the scan-converted digital ultrasound image data.

The signal processor 295 performs RGB processing on the image-processed ultrasound image data and transmits resultant data to the display 280 so that the image-processed digital ultrasound image data may be displayed in the form of an ultrasound image.

The display 280 may display a generated ultrasound image and various information processed by the ultrasound diagnostic apparatus 1. The ultrasound diagnostic apparatus 1 may include one or more display units 280-1 and 280-2 according to an embodiment. The display unit 280 may be coupled with a touch panel to form a touch screen.

The input device 270 receives a command input from a user to control the ultrasound diagnostic apparatus 1. For example, a user input may include, but is not limited to, an input to manipulate a button, a keypad, a mouse, a track ball, a jog switch, a knop or the like, an input to touch a touch pad or a touch screen, a voice input, a motion input, a biometric input (e.g., iris recognition, fingerprint recognition or the like), and the like.

The ultrasound diagnostic apparatus 1 may further include other components that are not described above with reference to FIGS. 5 and 6, and the relative positions of components may be changed according to the performance or configuration of the system.

Figure 7A:
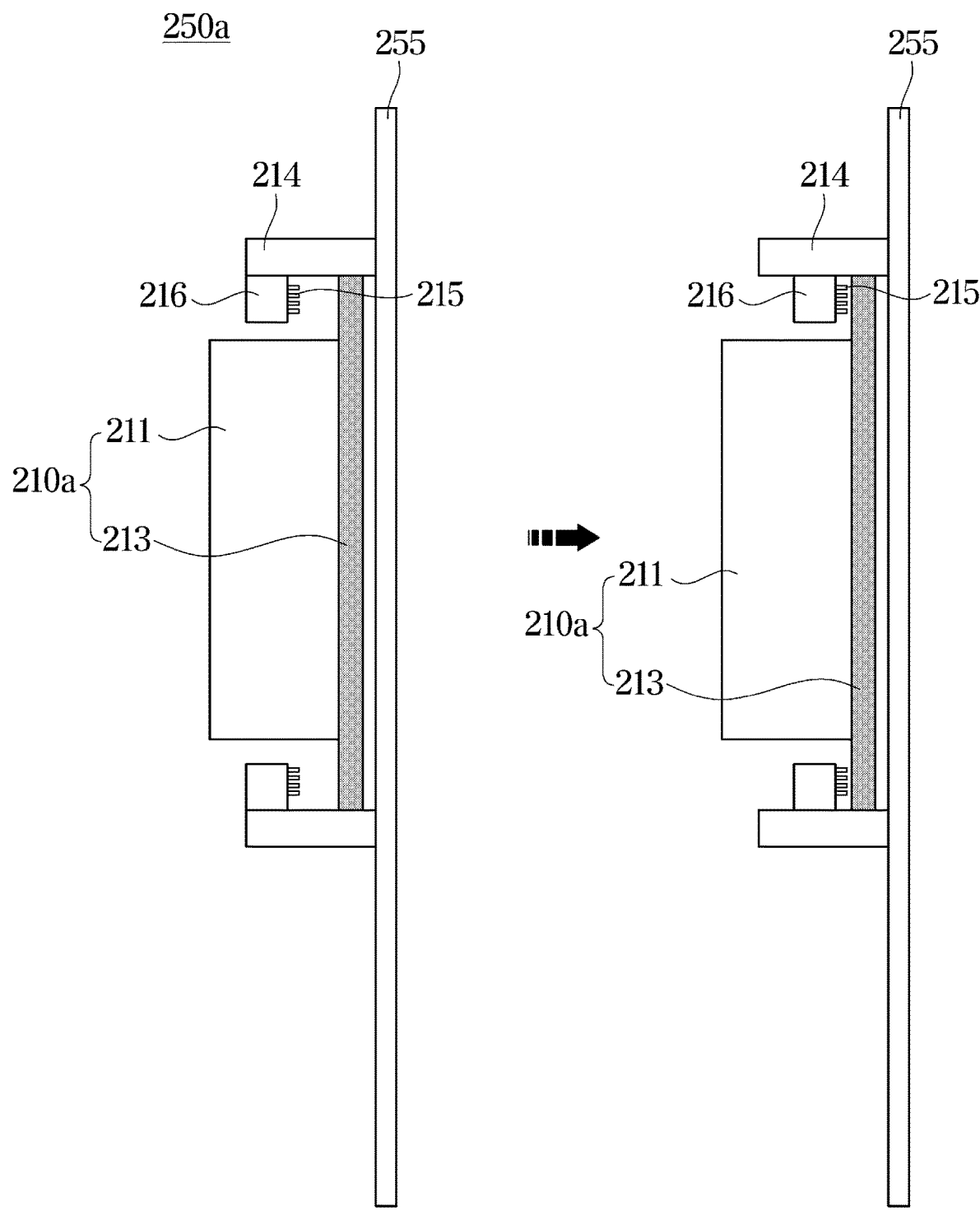
FIG. 7A is a diagram illustrating an operation of a connection module according to an embodiment.
Figure 7B:
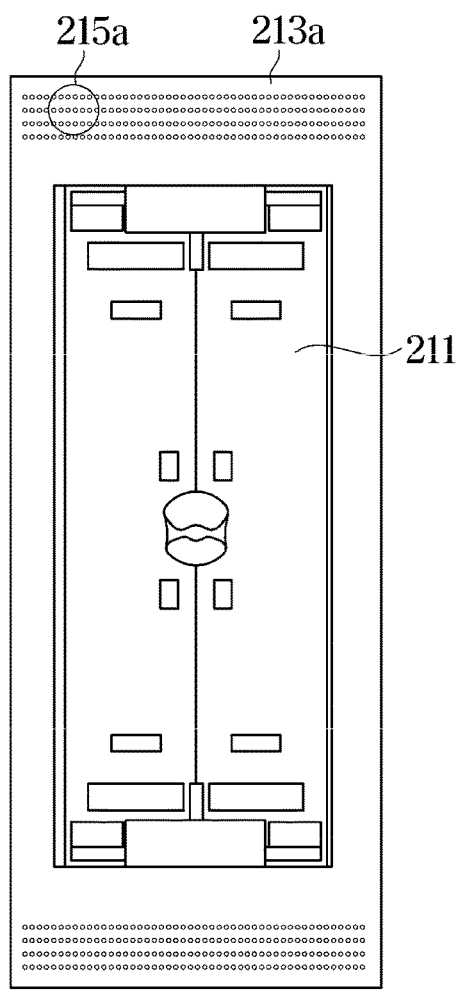
FIG. 7B is a schematic view of a front surface and a rear surface of a first printed circuit board (PCB) according to the embodiment of FIG. 7A.
Figure 7B:
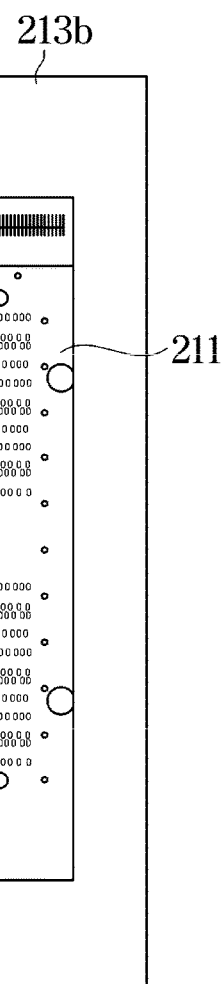

FIG. 7A is a diagram illustrating an operation of a connection module according to an embodiment. FIG. 7B is a schematic view of a front surface and a rear surface of a first printed circuit board (PCB) according to the embodiment of FIG. 7A.

Referring to FIG. 7A, a PSA board 250a according to an embodiment may be provided by coupling a moving part 216 and a connection pin 215 to each other. Specifically, when the controller 260 instructs to connect the probe 100 selected by a user, the moving part 216 may be moved to a first PCB 213. The connection pin 215 coupled to the first PCB 213 through the movement of the moving part 216 forms a point of contact with the first PCB 213.

When the connection pin 215 forms an electrical point of contact with the first PCB 213, an ultrasound signal transmitted from the probe 100 is sequentially transmitted to a female connector 211, the first PCB 213, the connection pin 215, a connection module 214, and a second PCB 255. Similarly, a control signal transmitted from the controller 260 is sequentially transmitted to the second PCB 255, the connection module 214, the connection pin 215, the first PCB 213, and the female connector 211.

Referring to FIG. 7B, a front surface 213a of a first PCB, which is included in a probe connection module 210a to be connected to the PSA board 250a according to an embodiment, is provided with a point of contact 215a with which the connection pin 215 of the moving part 216 may be brought into contact. When the moving part 216 is moved as shown in FIG. 7A, the connection pin 215 is in contact with the point of contact 215a on the front surface 213a of the first PCB.

An arrangement of the points of contact 215a on the front surface 213 of the first PCB may correspond to a shape of a line 215 on the moving part 216 and may include various arrangement forms.

Figure 8A:
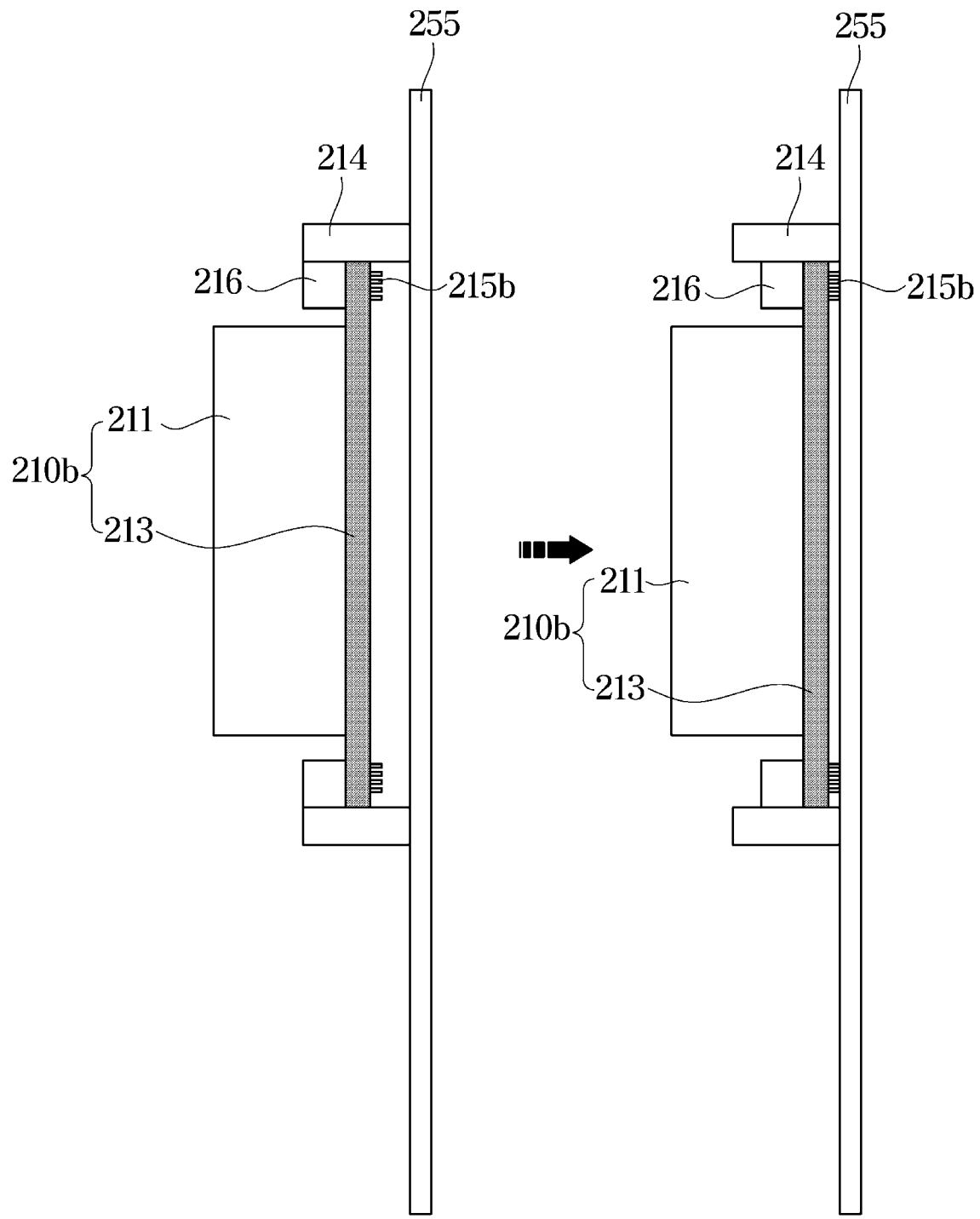
FIG. 8A is a diagram illustrating an operation of a connection module according to another embodiment.
Figure 8B:
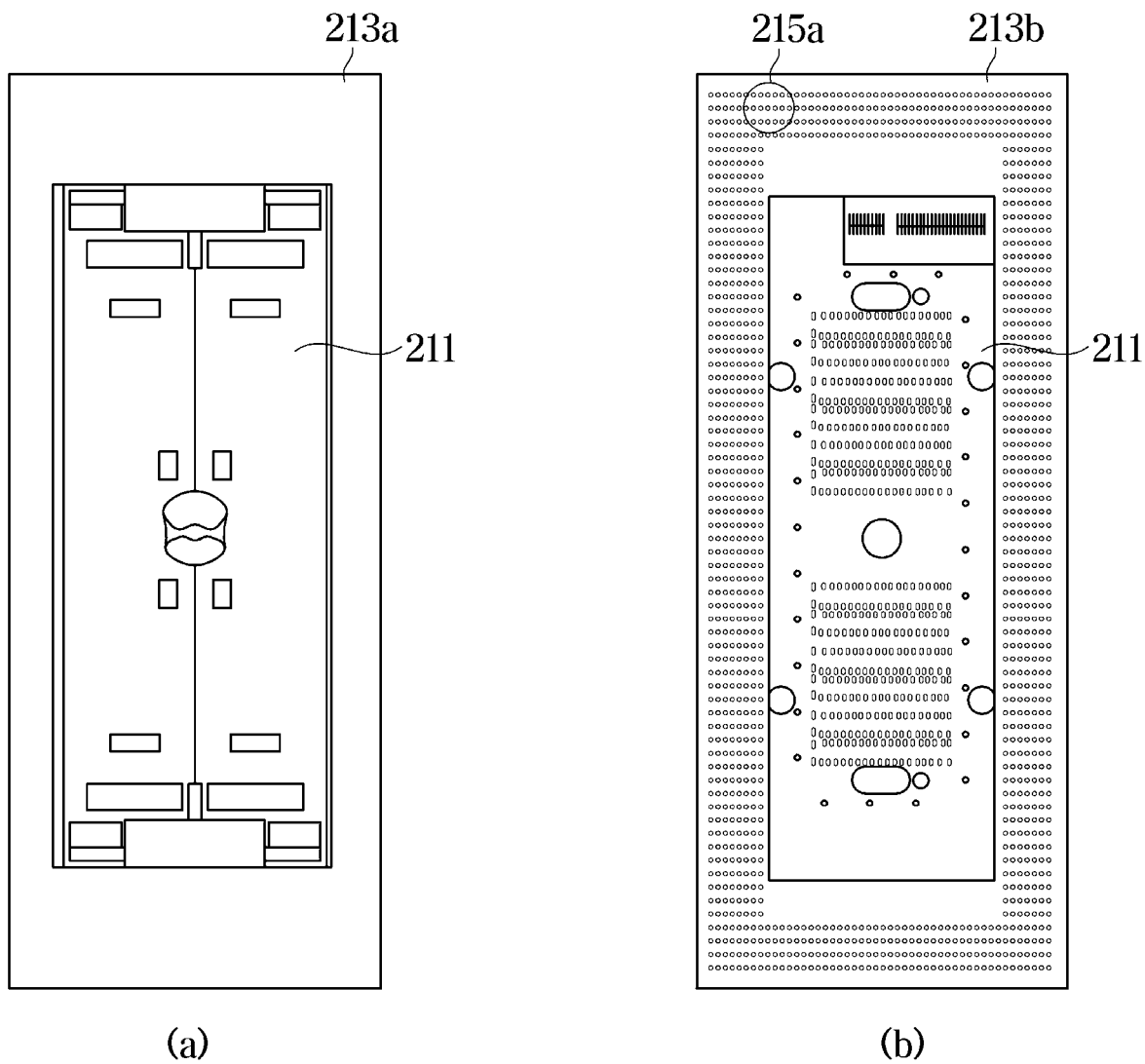
FIG. 8B is a schematic view of a front surface and a rear surface of a first PCB according to the embodiment of FIG. 8A.

FIG. 8A is a diagram illustrating an operation of a connection module according to another embodiment, and FIG. 8B is a schematic view of a front surface and a rear surface of a first PCB according to the embodiment of FIG. 8A. FIGS. 8A and 8B will be described together below to avoid a redundant description.

Referring to FIG. 8A, in a PSA board 250b according to another embodiment, the connection pin 215 may not be included in a moving part 216. That is, in the PSA board 250b according to the other embodiment, a probe connection module 210b may be moved directly to be brought into contact with a second PCB 255.

In the present embodiment, a connection pin 215b of the probe connection module 210b may be provided on a rear surface 213b of a first PCB 213. The moving part 216 allows the first PCB 213 to be moved to the second PCB 255, and thus the connection pin 215b forms an electrical point of contact with the second PCB 255.

Figure 9A:
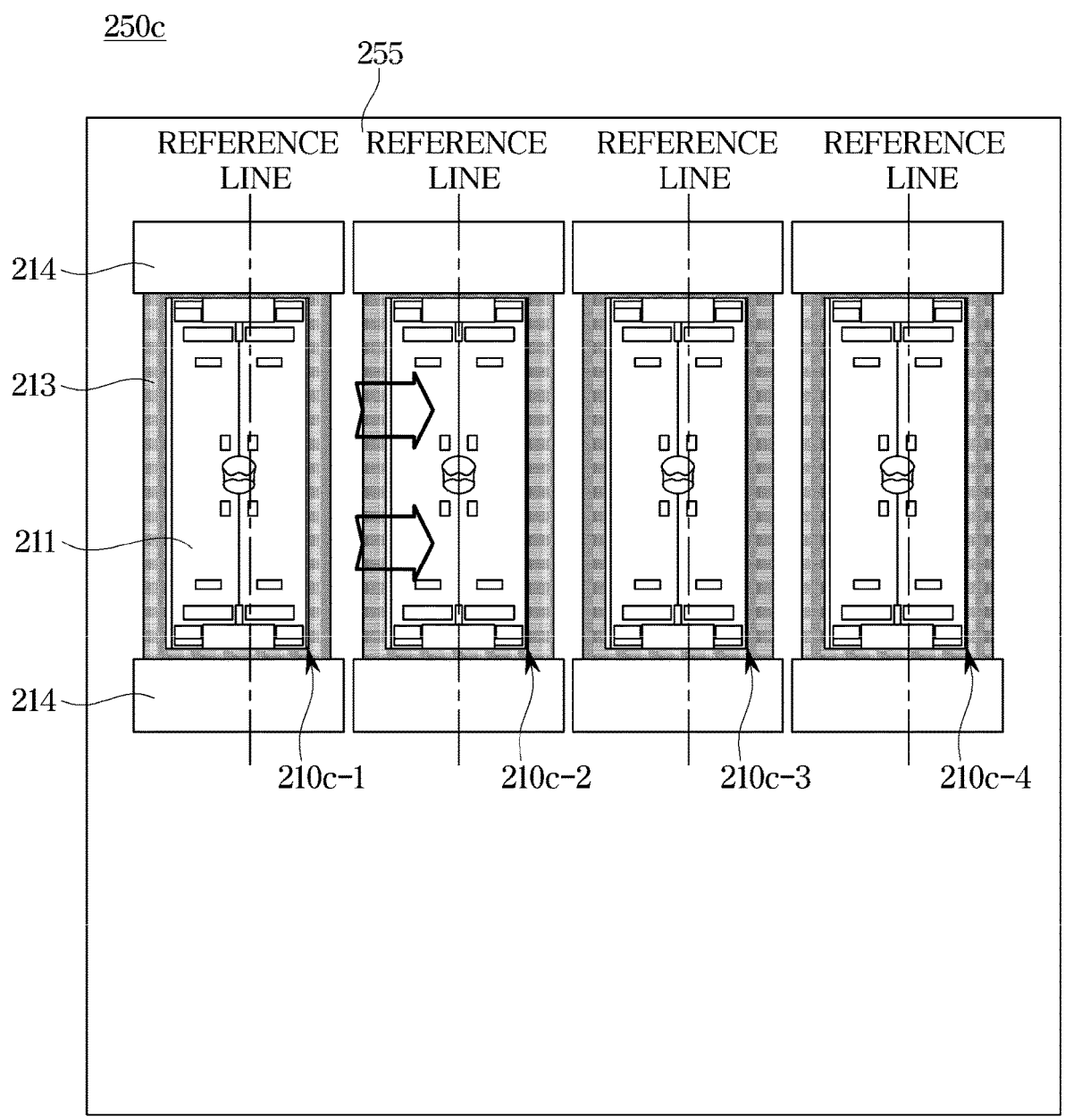
FIG. 9A is a diagram for describing a PSA board according to another embodiment.
Figure 9B:
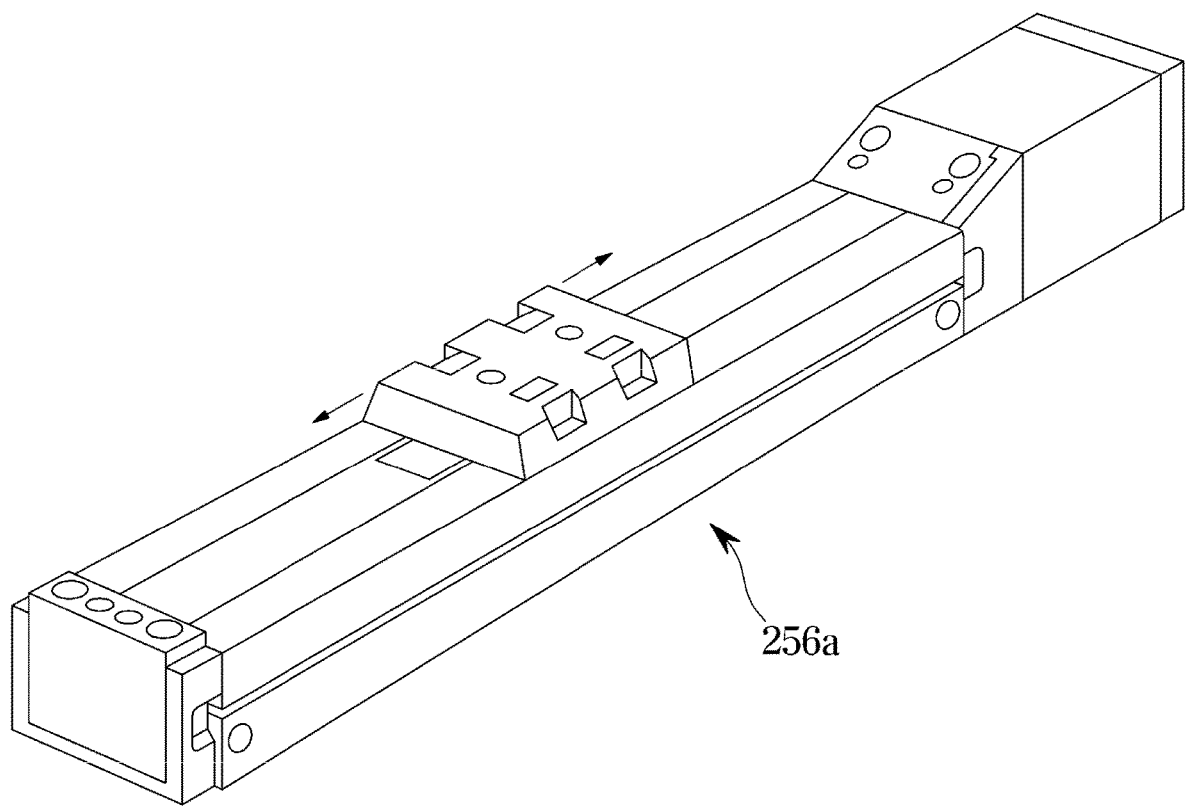
FIG. 9B is a schematic diagram of an actuator for operating the embodiment of FIG. 9A.
Figure 9C:
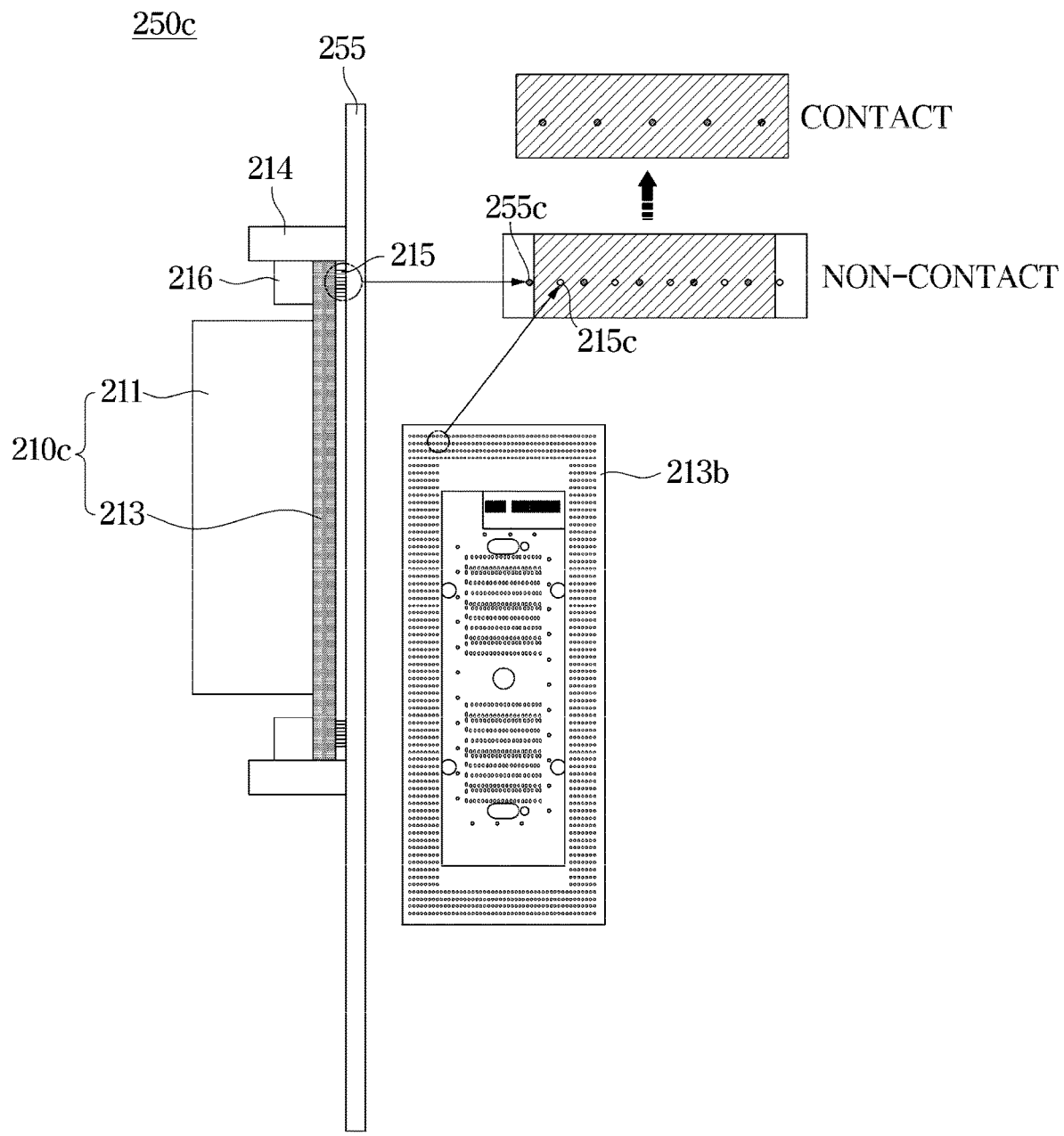
FIG. 9C is a side view of the embodiment of FIG. 9A.

FIG. 9A is a diagram for describing a PSA board according to another embodiment. FIG. 9B is a schematic diagram of an actuator for operating the embodiment of FIG. 9A. FIG. 9C is a side view of the embodiment of FIG. 9A. FIGS. 9A and 9B will be described together below to avoid a redundant description.

In a PSA board 250c according to another embodiment, a connection module 214 may allow a probe connection module 210c to be in contact with the second PCB 255 by moving the probe connection module 210c to a left or right side.

As shown in FIG. 9A, four probe connection modules 210c-1, 210c-2, 210c-3 and 210c-4 may be mounted on the PSA board 250c. When a user selects a probe 100 connected to the second probe connection module 210c-2 from among the four probe connection modules 210c-1, 210c-2, 210c-3 and 210c-4, the controller 260 may move the second probe connection module 210c-2 to a side to face toward a reference line.

Specifically, the PSA board 250c according to the present embodiment may include an actuator 256a as shown in FIG. 9B and may move the second probe connection module 210c-2 to a side.

Referring to FIG. 9C, in the present embodiment, in the probe connection module 210c, a point of contact 215c on a connection pin 215 provided on a rear surface 213b of a first PCB 213 and a point of contact 255a on a second PCB are not in contact with each other before the actuator 256a is operated.

The probe connection module 210c may be moved by operating the actuator 256a, and the connection pin 215 on the rear surface 213b of the first PCB 213 and the point of contact 255a on the second PCB may form a point of contact together.

The actuator is not limited to the actuator 256a according to the embodiment of FIG. 9B and may be manufactured in a form suitable for an embodiment. Another embodiment of an actuator will be described with reference to other drawings below.

Figure 10A:
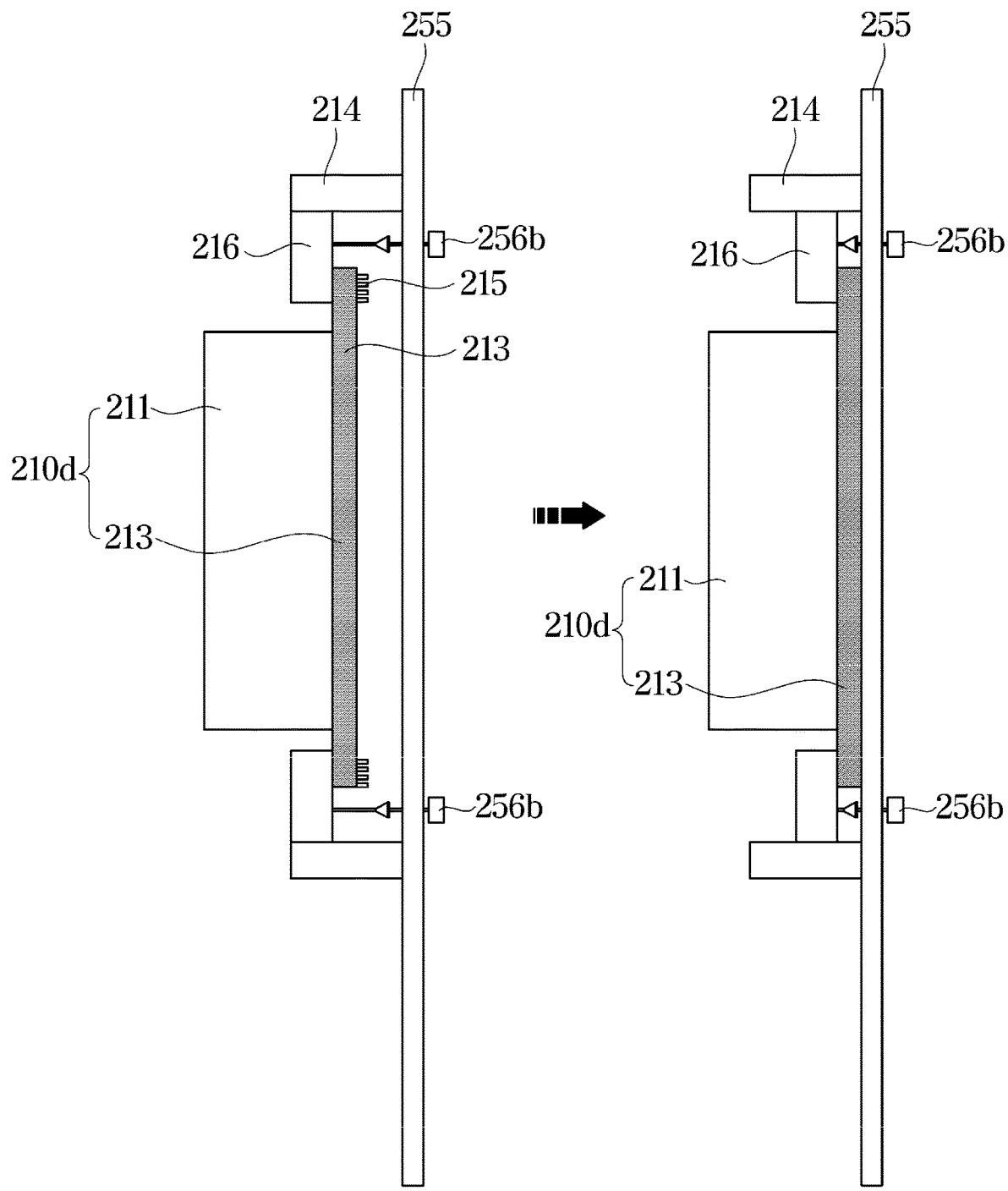
FIGS. 10A and 10B are diagrams for describing actuators according to other embodiments.
Figure 10B:
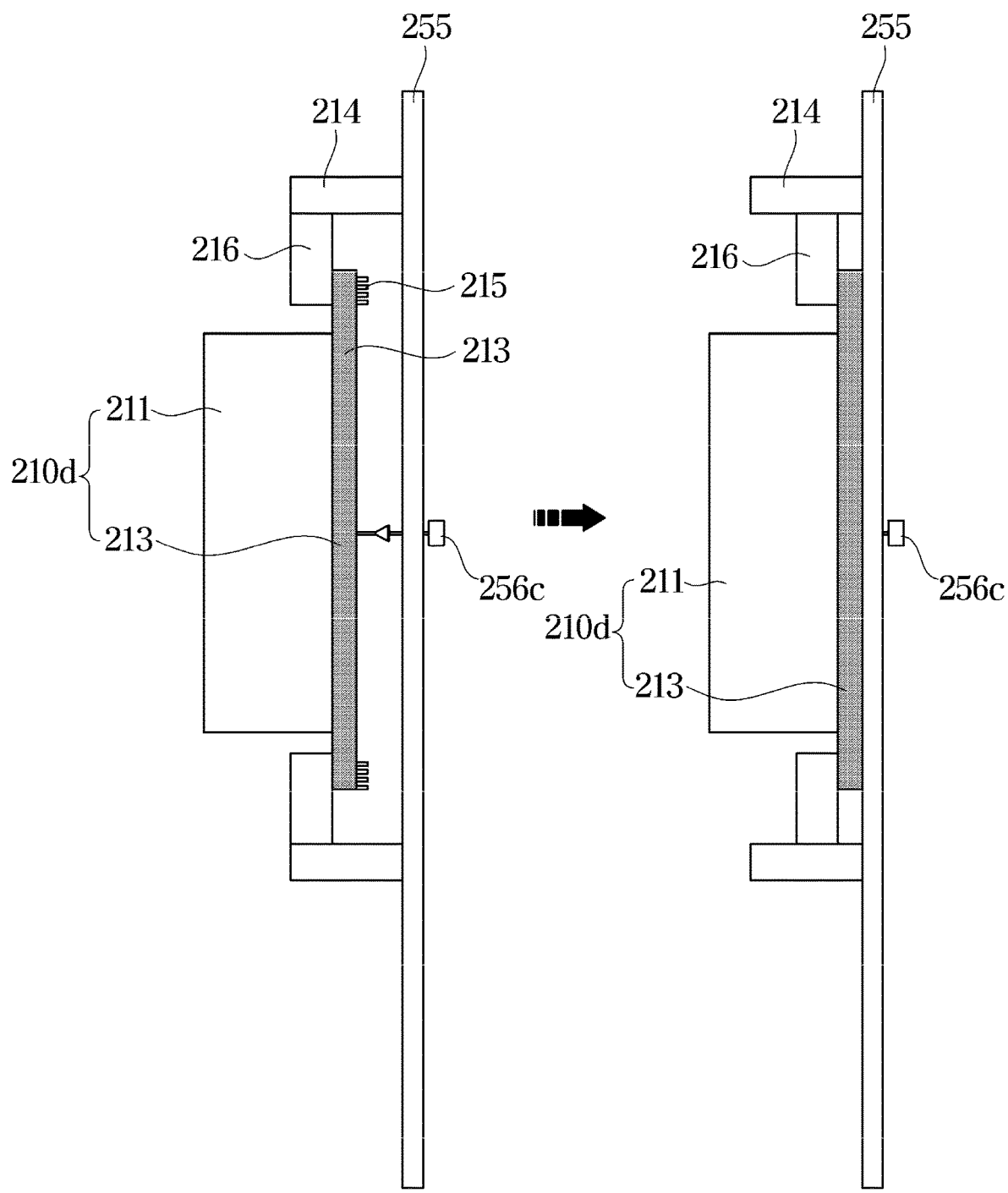

FIGS. 10A and 10B are diagrams for describing actuators according to other embodiments.

Referring to FIGS. 10A and 10B, in PSA boards 250d and 250e according to the embodiments, actuators 256b and 256c may be used to bring a probe connection module 210d into contact with a second PCB 255.

As shown in FIG. 10A, the actuator 256b may be provided on the second PCB 255 and may move a moving part 216. In the embodiment, the actuator 256b may bring the probe connection module 210d and the second PCB 255 into electrical contact with each other while moving the moving part 216.

As shown in FIG. 10B, the actuator 256c may be provided on the second PCB 255 and may move the probe connection module 210d. In the embodiment, the actuator 256c may bring the probe connection module 210d and the second PCB 255 into electrical contact with each other while directly moving the probe connection module 210d. In this case, a moving part 216 may also be moved together.

In the probe connection module 210*d* illustrated in FIGS. 10A and 10B, a connection pin 215 is provided on a rear surface of a first PCB 213 but embodiments are not limited thereto.

Figure 11A:
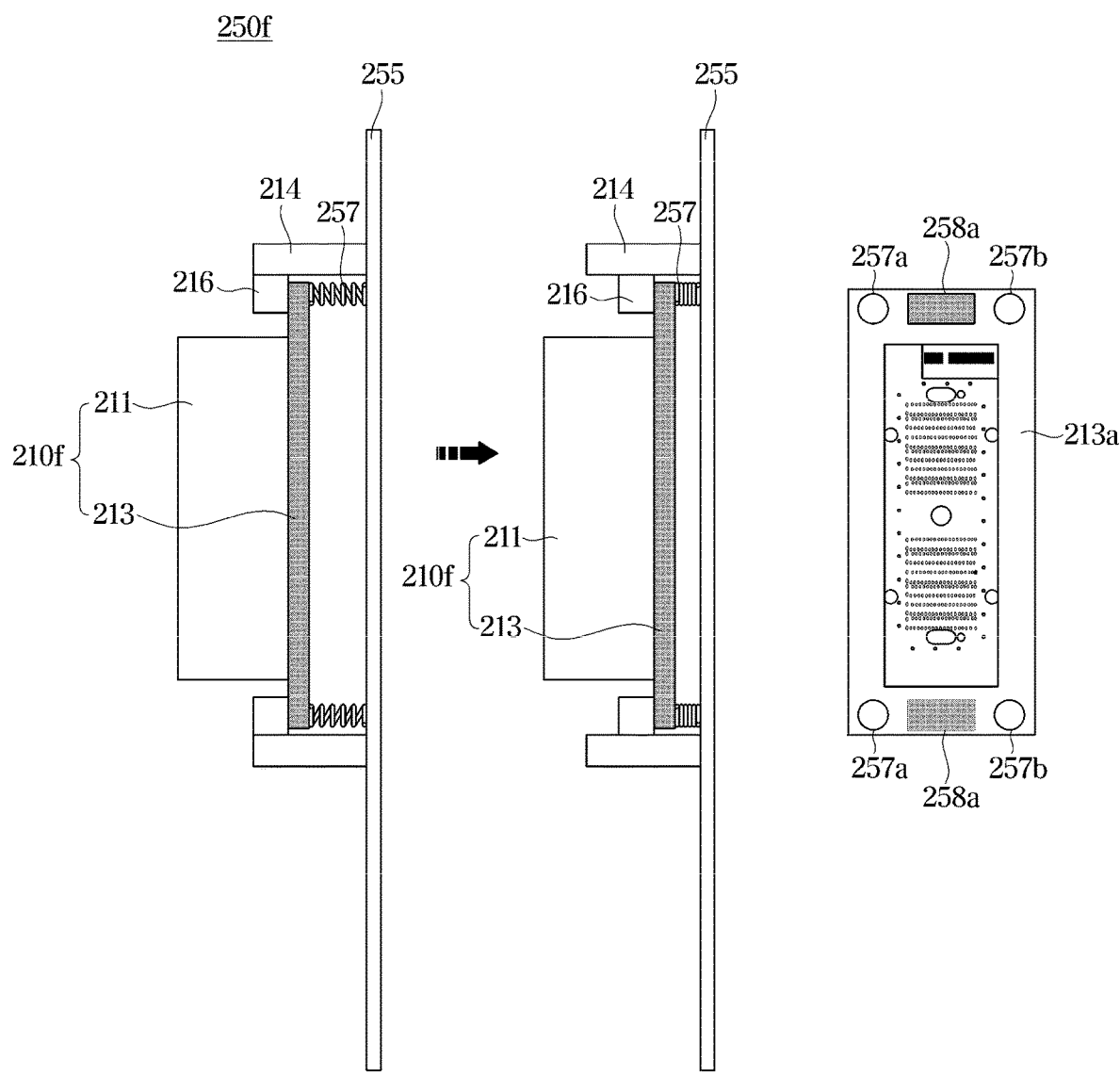
FIGS. 11A and 11B are diagrams for describing PSA boards including a spring according to embodiments.
Figure 11B:
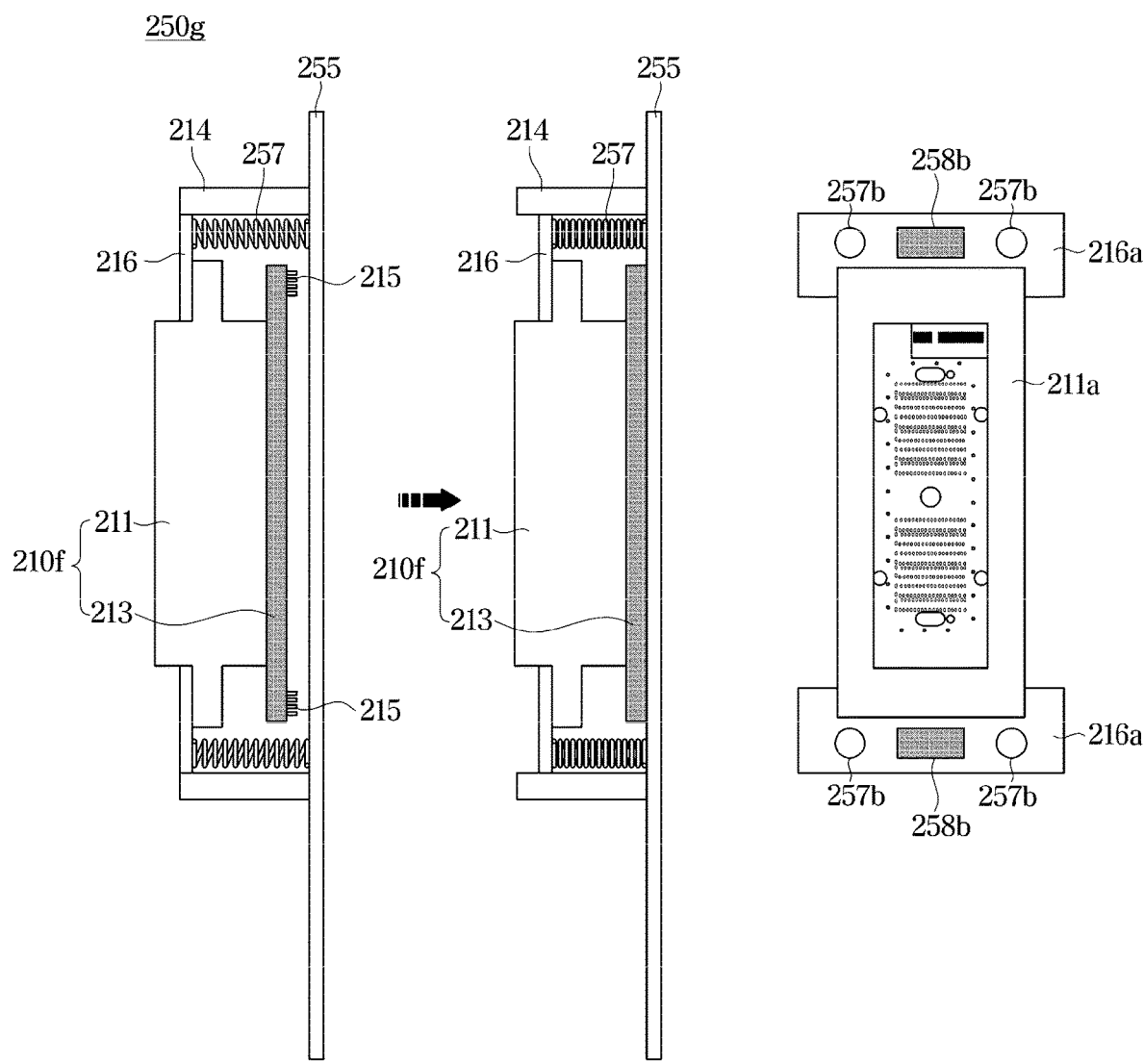

FIGS. 11A and 11B are diagrams for describing PSA boards including a spring according to embodiments.

Referring to FIGS. 11A and 11B, a PSA board 250*f* according to the embodiment may include a spring 257 for supporting probe connection modules 210*e* and 210*f*, and an electromagnet 258*a* and 258*b* for moving the probe connection modules 210*e* and 210*f*.

Specifically, the PSA board 250*f* may be electrically connected to the probe connection modules 210*e* and 210*f* through the electromagnet 258 provided on the second PCB 255. Therefore, the spring 257 may be provided to separate the probe connection modules 210*e* and 210*f* and the second PCB 255 before the probe connection modules 210*e* and 210*f* and the second PCB 255 are brought into contact with each other through the electromagnet 258.

As shown in FIG. 11A, the PSA board 250*f* according to an embodiment may include the spring 257 on the second PCB 255 to support the probe connection module 210*e*. The spring 257 may support a region 257*a* displayed on a rear surface 213*a* of a first PCB 213.

The rear surface 213*a* of the first PCB 213 may be provided with an electromagnet 258*a* with opposite polarity to that of the electromagnet 258 on the second PCB 255. When the electromagnet 258*a* is operated, the probe connection module 210*e* may be brought into contact with the second PCB 255, and the spring 257 and the moving part 216 may be moved together. After electrical connection, the controller 260 may control the probe 100.

As shown in FIG. 11B, a spring 257 provided on the PSA board 250*g* may support a moving part 216. In this case, the spring 257 may be in contact with a region 257*b* of a rear surface 216*a* of the moving part 216, unlike in FIG. 11A.

In the present embodiment, an electromagnet 258*b* with opposite polarity to that of an electromagnet 258 provided on a second PCB 255 may be provided on the rear surface 216*a* of the moving part 216, and a probe connection module 210*f* and the second PCB 255 may be electrically connected by operating the electromagnet 258*b*.

Figure 12:
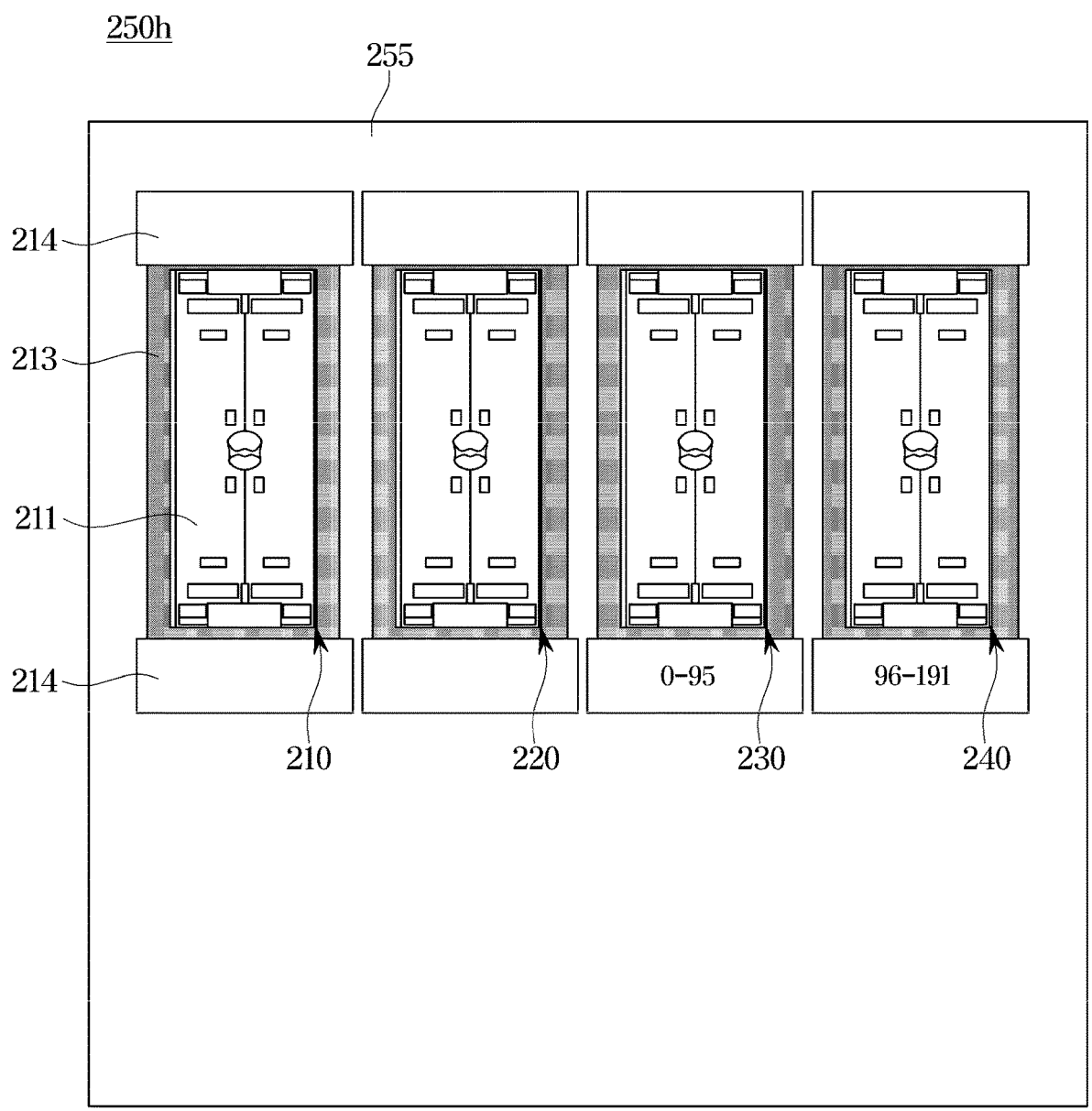
FIG. 12 is a diagram illustrating a situation in which a plurality of probe connection ports are connected.

FIG. 12 is a diagram illustrating a situation in which a plurality of probe connection ports are connected.

Referring to FIG. 12, a PSA board 250*h* according to an embodiment may be connected to at least two probes 100.

For example, one of the probes 100 may be locked to each of a third probe connection module 230 and a fourth probe connection module 240, and the ultrasound diagnostic apparatus 1 may receive a command to select both the probes 100 from a user. In this case, in the PSA board 250*h*, connection modules 214 included in the third probe connection module 230 and the fourth probe connection module 240 may be controlled to electrically connect the third and fourth probe connection modules 230 and 240 to a second PCB 255.

FIG. 12 illustrates an embodiment in which the two probe connection modules 230 and 240 are connected to the second PCB 255. In the PSA board 250*h*, elements of a transducer may be divided according to channels. For example, when two probes are connected in a system including 192 channels, in the PSA board 250*h*, only a 0th channel element to a 95th channel element may be connected to the third probe connection module 230 and only a 96th channel element to a 191th channel element may be divided and connected to the fourth probe connection module 240.

Elements of a transducer may be divided and connected into various numbers and according to various methods differently from those in FIG. 12.

Figure 13:
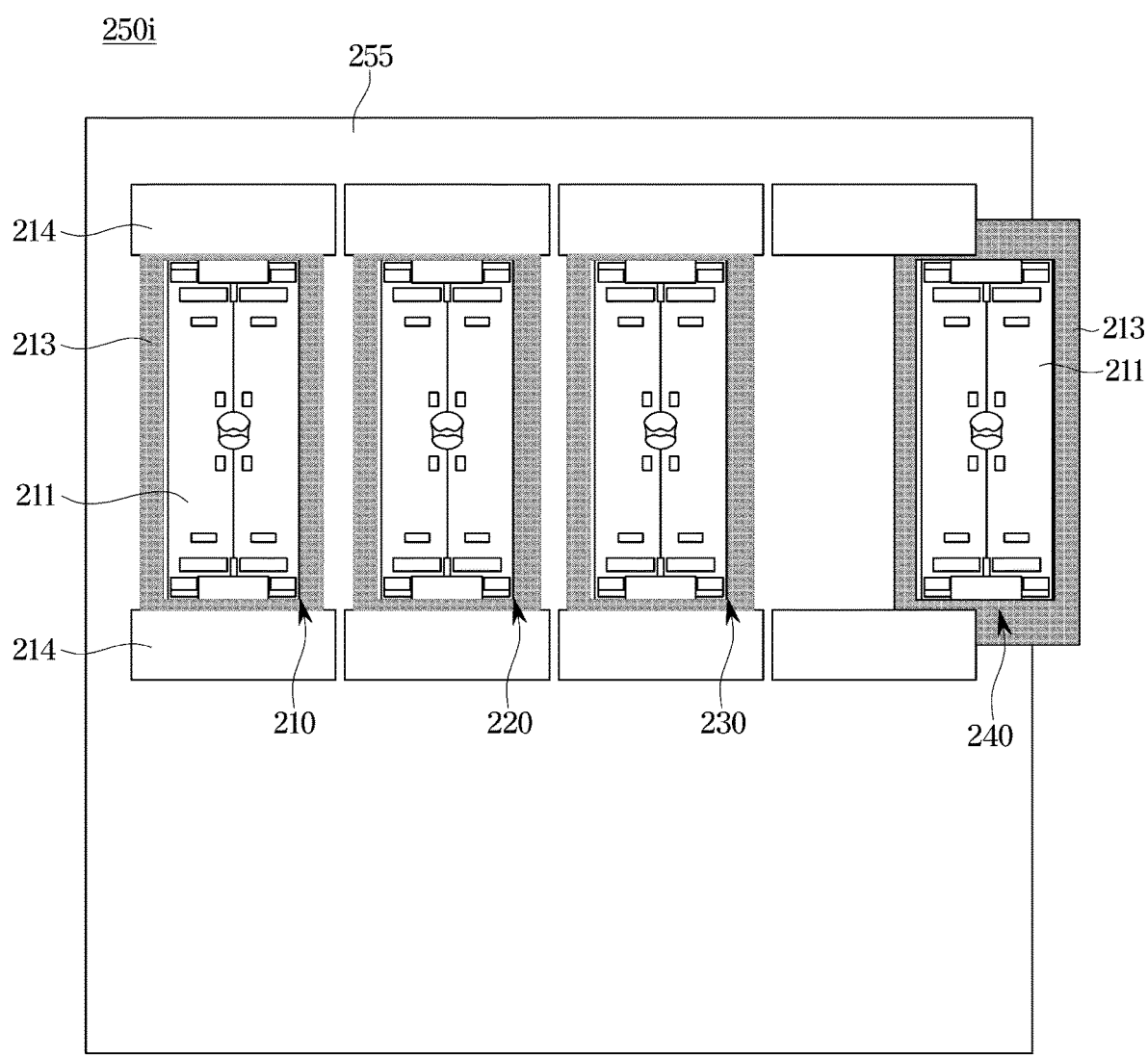
FIG. 13 is a diagram for describing compatibility of a PSA board according to an embodiment.

FIG. 13 is a diagram for describing compatibility of a PSA board according to an embodiment.

Referring to FIG. 13, the female connector 211, which is generally used, may be attached to probe connecting modules 210 to 240 to be connected to a PSA board 250*i*. Therefore, the PSA board 250*i* may be finally connected to the male connector 130 and the probe 100 which are generally used. Specifically, a user may select a probe connection module compatible with the probe 100 required for a diagnosis and the male connector 130 and thereafter mount the selected probe connection module on the PSA board 250*i*. The user may lock the female connector 211 of the selected probe connection module and the male connector 130 and electrically connect the selected probe connection module to a second PCB 255 of the PSA board 250*i* through the ultrasound diagnostic apparatus 1.

As shown in FIG. 13, the user may freely separate the fourth probe connection module 240 from the PSA board 250*i* and replace the fourth probe connection module 240 with another probe connection module.

Accordingly, the PSA boards 250*h* and 250*i* are easily connectable to the male connector 130 and the probe 100 as used in the related art and may be easily replaced when a probe connection port malfunctions, and channel elements may be divided and used for a plurality of probe connection modules, thereby improving compatibility.

Figure 14A:
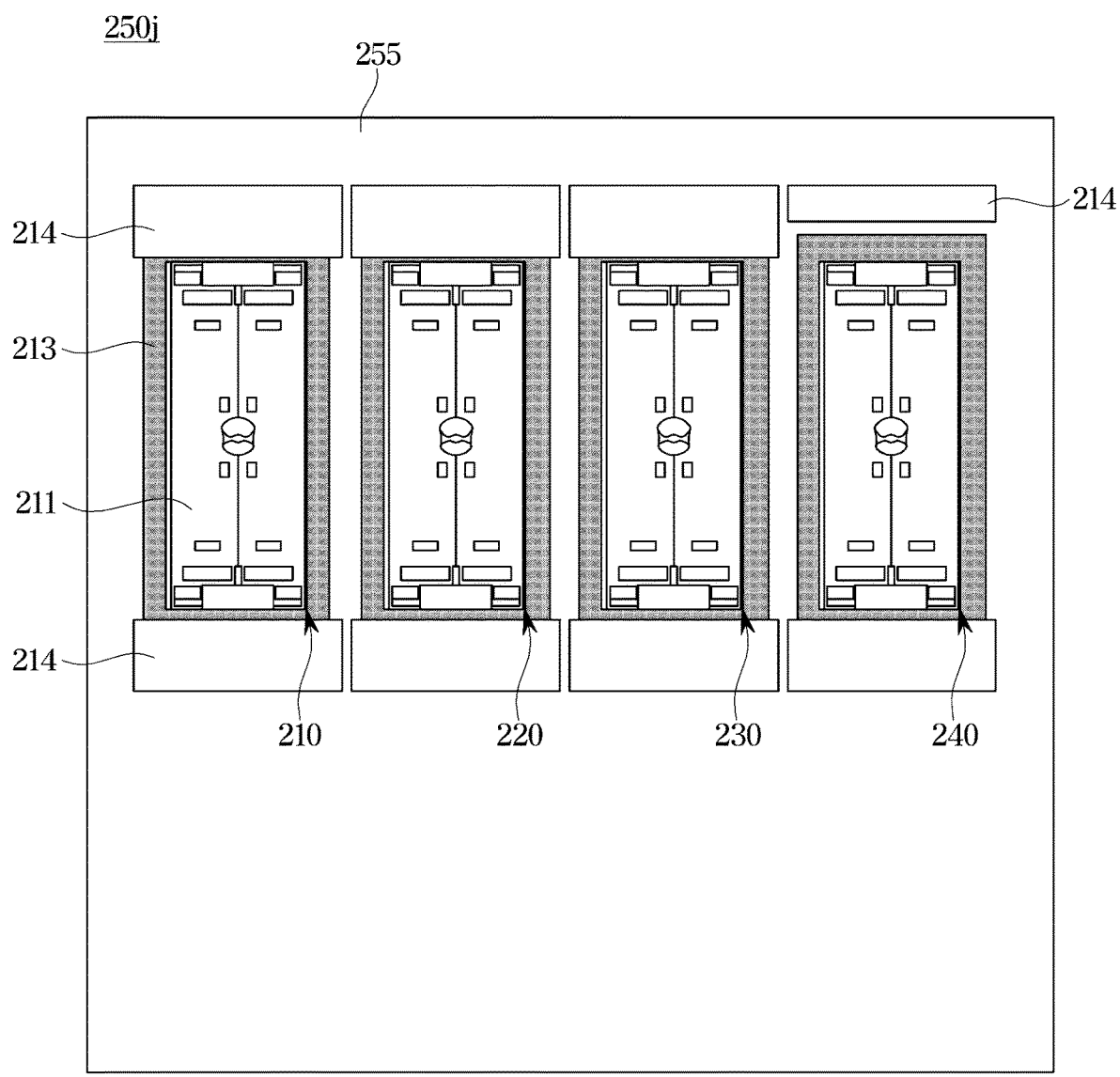
FIGS. 14A and 14B are diagrams illustrating replacing of a probe connection module according to embodiments.
Figure 14B:
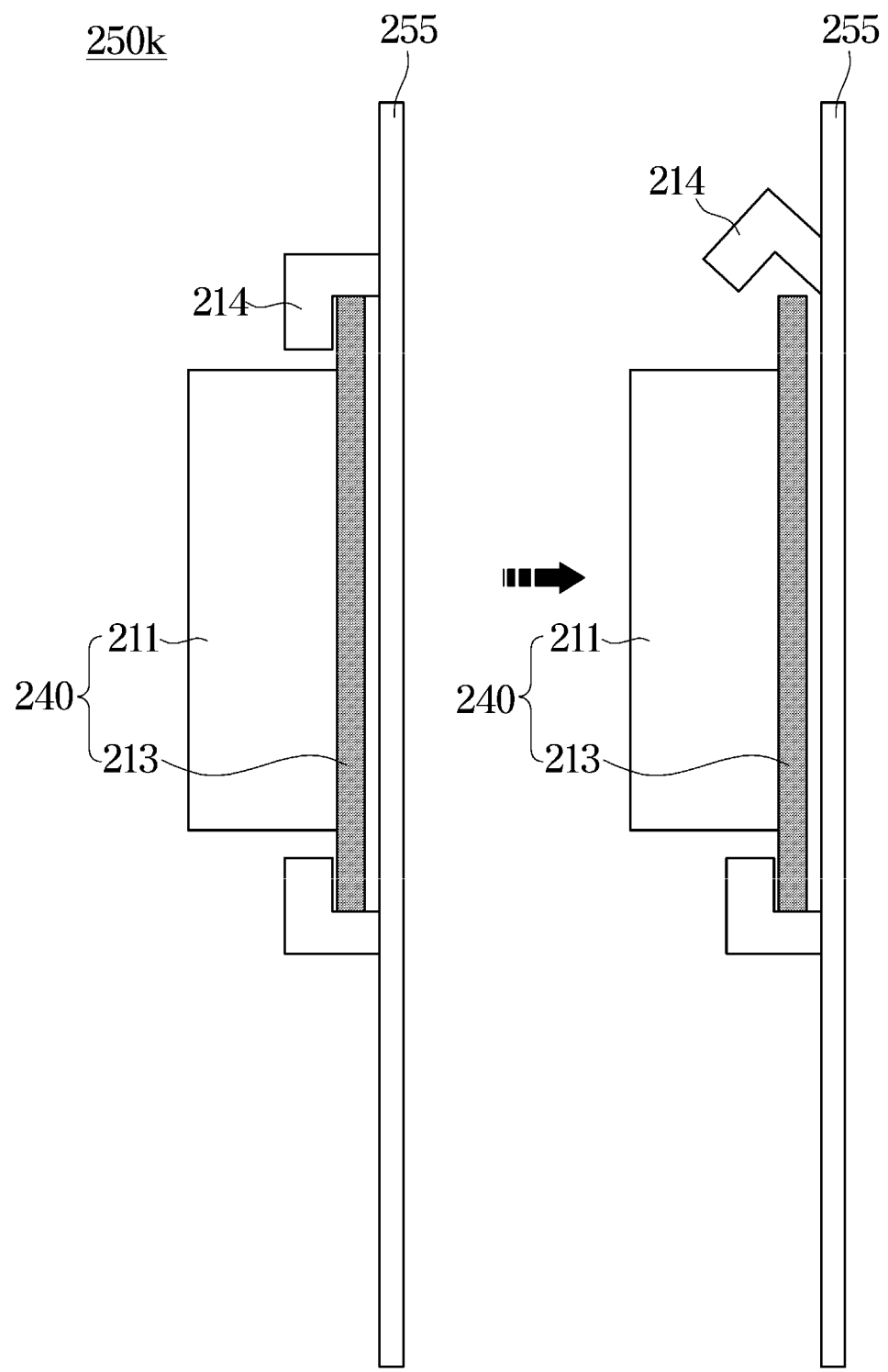

FIGS. 14A and 14B are diagrams illustrating replacing of a probe connection module according to embodiments.

As shown in FIG. 14A, in a PSA board 250*j*, a connection module 214 may be rotated to separate a fourth probe connection module 240.

As shown in FIG. 14B, one region of a connection module 214 may be fixed onto a second PCB 255 and another region thereof may be hinge-coupled to the second PCB 255 to be rotated within a predetermined radius. That is, the PSA board 250*j* includes the connection module 214 that is not fixed so that a user may easily separate the fourth probe connection module 240.

In the PSA board 250*j*, not only the fourth probe connection module 240 may be simply separated but also probe connection modules 210, 220 and 230 may be separated through the fourth probe connection module 240.

FIG. 15 is a flowchart of a control method of an ultrasound diagnostic apparatus according to an embodiment.

Referring to FIG. 15, the ultrasound diagnostic apparatus 1 receives recognition information from the probe 100 (300).

As described above with the drawings, the PSA board 250 provided in the ultrasound diagnostic apparatus 1 may include the connection module 214 for mounting a probe connection module thereon. Depending on the number of connection modules 214, a plurality of probe connection modules may be mounted simultaneously on the PSA board 250.

The probe connection module may include the female connector 211 and the first PCB 213, and the male connector 130 connected to the probe 100 may be inserted into the female connector 211. For example, when the insertion of the male connector 130 into the female connector 211 is sensed, the probe 100 may transmit the recognition information to the main body 200.

The recognition information refers to information related to the probe 100 and may include, for example, probe identification information such as probe model information, version information, and a serial number. The recognition information may be transmitted to the recognition information receiving unit 212 of the main body 200 through the recognition information transmitting unit 140 included in the probe 100 in the wireless communication manner.

When the recognition information is received, the main body 200 may identify connection of a current probe connection module to the probe 100 and display the recognition information on the display 280.

However, the recognition information is not necessarily transmitted to the main body 200 only when the probe 100 is connected to the probe connection module. As another example, the recognition information may be transmitted when the probe 100 is located within a predetermined distance from the main body 200 regardless of the connection of the probe 100 to the probe connection module.

The ultrasound diagnostic apparatus 1 receives a selection signal with respect to the probe 100 from a user (310).

The ultrasound diagnostic apparatus 1 may display a user interface inducing a user to select the probe 100 after the received recognition information is displayed on the display 280.

The ultrasound diagnostic apparatus 1 electrically connects the probe connection module and the second PCB 255 on the basis of the selection signal (320).

There may be various embodiments in which the PSA board 250 connects the probe connection module and the second PCB 255. Specifically, the PSA board 250 may electrically connect the first PCB 213 and the second PCB 255 through the connection pin 215 provided on the connection module 214 included in the PSA board 250 or may move the probe connection module through the connection module 214 to electrically connect the first PCB 213 and the second PCB 255.

When the PSA board 250 electrically connects the first PCB 213 and the second PCB 255 on the basis of a selection signal input from a user, the probe connection module functions as a path for transmitting an ultrasound signal transmitted from the probe 100 to the beamformer 290.

The ultrasound diagnostic apparatus 1 receives an ultrasound signal from the second PCB 255 (330).

When the probe connection module is connected to the second PCB 255, the ultrasound diagnostic apparatus 1 may control the probe 100. The ultrasound diagnostic apparatus 1 may control the probe 100 to transmit an ultrasound signal to a subject and receives an echo ultrasound signal received by the probe 100.

The ultrasound diagnostic apparatus 1 generates an ultrasound image on the basis of the received ultrasound signal (340).

An ultrasound image may be generated from an ultrasound signal by the ultrasound diagnostic apparatus 1 in various ways. In addition, the ultrasound diagnostic apparatus 1 may display the generated ultrasound image on the display 280 and provide a variety of interfaces for adjusting an ultrasound image generated by a user.

Therefore, in the ultrasound diagnostic apparatus 1, the probe 100, which is generally used in the related art, and a probe connection module compatible with a connector provided in the probe 100 are used and thus a relay used in the related art may be omitted. In addition, in the ultrasound diagnostic apparatus 1, the relay may be omitted to reduce design complexity, and utilization of a space, which is occupied by relays in the case of the related art, may be increased.

The invention claimed is:

1. An ultrasound diagnostic apparatus comprising:
   a recognition information receiver configured to receive recognition information from a probe;
   an input device configured to receive a selection signal with respect to the probe from a user;
   a probe connection module comprising a first connector configured to lock and hold a second connector of the probe to be connected to the second connector, and a sub PCB to which the first connector is attached;
   a probe select assembly (PSA) board including a connection module configured to mount the probe connection module thereon and a main printed circuit board (PCB) configured to be electrically connected to the probe connection module; and
   a controller configured to control the PSA board to connect the probe connection module to the main PCB on the basis of the selection signal and control the probe on the basis of a connection between the probe connection module and the main PCB,
   wherein the connection module comprises:
      a first connection pin configured to allow the connection module to be electrically connected to the sub PCB when the first connection pin is in contact with the sub PCB; and
      a moving part configured to move the first connection pin to a first location at which the first connection pin is in contact with the sub PCB or a second location at which the first connection pin is not in contact with the sub PCB,
   wherein the probe connection module is detachable from the PSA board, and
   wherein the controller is configured to control the moving part to move the first connection pin so that the first connection pin is in contact with the sub PCB based on the selection signal.

2. The ultrasound diagnostic apparatus of claim 1, wherein the moving part comprises an actuator configured to move the first connection pin.

3. The ultrasound diagnostic apparatus of claim 2, wherein the actuator is provided on the PSA board and configured to move the probe connection module on the basis of at least one of an electromagnet, a motor, hydraulic pressure, or pneumatic pressure.

4. The ultrasound diagnostic apparatus of claim 1, wherein the main PCB comprises a connection pin configured to allow the main PCB to be electrically connected to the sub PCB.

5. The ultrasound diagnostic apparatus of claim 1, wherein a sub PCB comprises a connection pin configured to allow the sub PCB to be electrically connected to the main PCB.

6. The ultrasound diagnostic apparatus of claim 1, wherein the main PCB has an area greater than or equal to an area of the sub PCB.

7. The ultrasound diagnostic apparatus of claim 1, wherein the connection module is provided to be rotated on the main PCB to separate the probe connection module.

8. The ultrasound diagnostic apparatus of claim 1, wherein the controller divides and connects channel elements on the basis of a plurality of pieces of recognition information.

9. The ultrasound diagnostic apparatus of claim 1, further comprising
   a display configured to display the recognition information, wherein the controller controls the display to display the recognition information.

10. The ultrasound diagnostic apparatus of claim 1, wherein the sub PCB has an area greater than or equal to an area of the first connector.

11. A control method of an ultrasound diagnostic apparatus, comprising:
    receiving a selection signal for selecting a probe from a user;
    controlling a probe select assembly (PSA) board to connect a probe connection module to a main printed circuit board (PCB) on the basis of the selection signal, the PSA board comprising a connection module configured to mount the probe connection module thereon and the main PCB configured to be electrically connected to the probe connection module;
    controlling the probe selected on the basis of a connection between the probe connection module and the main PCB; and
    receiving an ultrasound signal from the probe through the PSA board,
    wherein the probe connection module is mount on the connection module and comprises:
        a first connector configured to lock and hold a second connector of the probe to be connected to the second connector; and
        a sub PCB to which the first connector is attached,
    wherein the connection module comprises:
        a first connection pin configured to allow the connection module to be electrically connected to the sub PCB when the first connection pin is in contact with the sub PCB; and
        a moving part configured to move the first connection pin to a first location at which the first connection pin is in contact with the sub PCB or a second location at which the first connection pin is not in contact with the sub PCB,
    wherein the probe connection module is detachable from the PSA board, and
    wherein controlling the PSA board comprises controlling the moving part to move the first connection pin so that the first connection pin is in contact with the sub PCB based on the selection signal.

\* \* \* \* \*